US007662382B2

(12) United States Patent
Cosgrove

(10) Patent No.: US 7,662,382 B2
(45) Date of Patent: Feb. 16, 2010

(54) INDUCIBLE LIGAND FOR α1β1 INTEGRIN AND USES

(75) Inventor: Dominic Cosgrove, Omaha, NE (US)

(73) Assignee: Boys Town National Research Hospital, Omaha, NE (US)

( * ) Notice: Subject to any disclaimer, the term of this patent is extended or adjusted under 35 U.S.C. 154(b) by 120 days.

(21) Appl. No.: 12/069,297

(22) Filed: Feb. 8, 2008

(65) Prior Publication Data

US 2008/0227121 A1    Sep. 18, 2008

Related U.S. Application Data

(62) Division of application No. 10/698,121, filed on Oct. 31, 2003, now Pat. No. 7,348,002.

(60) Provisional application No. 60/423,297, filed on Nov. 1, 2002.

(51) Int. Cl.
    *C07K 16/28*    (2006.01)
    *A61K 39/395*   (2006.01)

(52) U.S. Cl. .............................. 424/145.1; 530/388.23; 530/388.24

(58) Field of Classification Search ........................ None
See application file for complete search history.

(56) References Cited

U.S. PATENT DOCUMENTS

| | | | |
|---|---|---|---|
| 5,567,440 A | 10/1996 | Hubbell et al. | |
| 5,788,966 A | 8/1998 | Chess et al. | |
| 6,492,325 B1 | 12/2002 | Cosgrove | |
| 6,955,810 B2 | 10/2005 | Gotwals et al. | |
| 7,348,002 B2 * | 3/2008 | Cosgrove | ................. 424/133.1 |

FOREIGN PATENT DOCUMENTS

| | | | |
|---|---|---|---|
| WO | WO 99/61040 A2 | 12/1999 | |
| WO | WO 99/61040 A3 | 1/2000 | |

OTHER PUBLICATIONS

Abraham et al., "A monoclonal antibody to α1β1 blocks antigen-induced airway responses in sheep," Jan. 1, 2004. *American Journal of Respiratory Critical Care Medicine* 169(1):97-104.
Adams et al., "Initial assessment of human gene diversity and expression patterns based upon 83 million nucleotides of cDNA sequence," Sep. 28, 1995. *Nature* 377(6547 Suppl.):3-174.
Andreasen et al., "Expression and functional importance of collagen-binding integrins, α1β1 and α2β1, on virus-activated T cells," 2003 *The Journal of Immunology* 171:2804-2811.
Bank et al., "Lymphocytes expressing α1β1 integrin (very late antigen-1) in peripheral blood of patients with arthritis are a subset of CD45RO+ T-Cells primed for rapid adhesion to collagen IV," Dec. 2002. *Clinical Immunology* 105(3):247-258.
Border et al., "Suppression of experimental glomerulonephritis by antiserum against transforming growth factor β1," Jul. 26, 1990. *Nature* 346:371-374.

Branch, "A good antisense molecule is hard to find," Feb. 1998. *Trends in Biochemical Science* 23(2):45-50.
Conti and DiGioacchino, "MCP-1 and RANTES are mediators of acute and chronic inflammation," May-Jun. 2001. *Allergy and Asthma Proc.* 22(3):133-137.
Cook et al., "Treatment with an antibody to VLA-1 integrin reduces glomerular and tubulointerstitial scarring in a rat model of crescentic glomerulonephritis," Oct. 2002. *American Journal of Pathology* 161(4):1265-1272.
Cosgrove, Dominic; "Molecular aspects of Alport renal disease progression," Grant Abstract, Grant No. 1RO1DK055000-01 [online]. National Institute of Diabetes and Digestive and Kidney Disease, National Institutes of Health. Project dates Apr. 15, 1999 to Mar. 31, 2003 [retrieved on May 2, 2008]. Retrieved from the Internet: <http://crisp.cit.nih.gov/crisp/CRISP_LIB.getdoc?textkey=2746599&p_grant_num=1R01DK055000-01&p_query=&ticket=63510999& p_audit_session_id=319533758&p_keywords=>; 2 pgs.
Cosgrove, Dominic; "Molecular aspects of Alport renal disease progression," Grant Abstract, Grant No. 5RO1DK055000-02 [online]. National Institute of Diabetes and Digestive and Kidney Disease, National Institutes of Health. Project dates Apr. 15, 1999 to Mar. 31, 2003 [retrieved on May 2, 2008]. Retrieved from the Internet: <http://crisp.cit.nih.gov/crisp/CRISP_LIB.getdoc?textkey=6177814&p_grant_num=5R01DK055000-02&p_query=&ticket=63510999& p_audit_session_id=319533758&p_keywords=>; 2 pgs.
Cosgrove, Dominic; "Molecular aspects of Alport renal disease progression," Grant Abstract, Grant No. 5RO1DK055000-03 [online]. National Institute of Diabetes and Digestive and Kidney Disease, National Institutes of Health. Project dates Apr. 15, 1999 to Mar. 31, 2003 [retrieved on May 2, 2008]. Retrieved from the Internet: <http://crisp.cit.nih.gov/crisp/CRISP_LIB.getdoc?textkey=6381443&p_grant_num=5R01DK055000-03&p_query=&ticket=63510999& p_audit_session_id=319533758&p_keywords=>; 2 pgs.
Cosgrove, Dominic; "Molecular aspects of Alport renal disease progression," Grant Abstract, Grant No. 5RO1DK055000-04 [online]. National Institute of Diabetes and Digestive and Kidney Disease, National Institutes of Health. Project dates Apr. 15, 1999 to Mar. 31, 2003 [retrieved on May 2, 2008]. Retrieved from the Internet: <http://crisp.cit.nih.gov/crisp/CRISP_LIB.getdoc?textkey=6517555&p_grant_num=5R01DK055000-04&p_query=&ticket=63510999& p_audit_session_id=319533758&p_keywords=>; 2 pgs.

(Continued)

*Primary Examiner*—Maher M Haddad
(74) *Attorney, Agent, or Firm*—Mueting, Raasch & Gebhardt, P.A.

(57) ABSTRACT

The present invention is directed to the identification and use of agents, particularly peptides and monoclonal antibodies that disrupt the interaction between Collagen XIII and α1β1 integrin.

6 Claims, 10 Drawing Sheets

OTHER PUBLICATIONS

Cosgrove, Dominic; "Molecular aspects of Alport renal disease progression," Grant Abstract, Grant No. 2RO1DK055000-05A3 [online]. National Institute of Diabetes and Digestive and Kidney Disease, National Institutes of Health. Project dates Apr. 15, 1999 to Mar. 31, 2009 [retrieved on May 2, 2008]. Retrieved from the Internet: <http://crisp.cit.nih.gov/crisp/CRISP_LIB.getdoc?textkey=6968892&p_grant_num=2R01DK055000-05A3& p_query=&ticket=63510999&p_audit_session_id=319533758& p_keywords=>; 2 pgs.

Cosgrove, Dominic; "Molecular aspects of Alport renal disease progression," Grant Abstract, Grant No. 5RO1DK055000-06 [online]. National Institute of Diabetes and Digestive and Kidney Disease, National Institutes of Health. Project dates Apr. 15, 1999 to Mar. 31, 2009 [retrieved on May 2, 2008]. Retrieved from the Internet: <http://crisp.cit.nih.gov/crisp/CRISP_LIB.getdoc?textkey=7118099&p_grant_num=5R01DK055000-06&p_query=&ticket=63510999& p_audit_session_id=319533758& p_keywords=>; 2 pgs.

Cosgrove, Dominic; "Molecular aspects of Alport renal disease progression," Grant Abstract, Grant No. 5R0IDK055000-07 [online]. National Institute of Diabetes and Digestive and Kidney Disease, National Institutes of Health. Project dates Apr. 15, 1999 to Mar. 31, 2003 [retrieved on May 2, 2008]. Retrieved from the Internet: <http://crisp.cit.nih.gov/crisp/CRISP_LIB.getdoc?textkey=7248757&p_grant_num=5R01DK055000-07&p_query=&ticket=63510999& p_audit_session_id=319533758& p_keywords=>; 2 pgs.

Cosgrove et al., "Integrin $\alpha1\beta1$ and transforming growth factor-$\beta1$ play distinct roles in Alport glomerular pathogenesis and serve as dual targets for metabolic therapy," Nov. 2000. *American Journal of Pathology* 157(5):1649-1659.

Cotran et al. (Eds), "Chapter 3: Acute and chronic inflammation," in *Robbins Pathologic Basis of Disease*. W.B. Saunders Company: Philadelphia, PA; 1999. Title page, publishers page, table of contents, and pp. 50-88.

De Fougerolles et al., "Regulation of inflammation by collagen-binding integrins $\alpha1\beta1$ and $\alpha2\beta1$ in models of hypersensitivity and arthritis," Mar. 2000. *The Journal of Clinical Investigation* 105(6):721-729.

Dennis et al., "$\alpha1\beta1$ Integrin Facilitates Monocyte Migration into the Tubulointerstitial Space of Fibrotic Kidneys in Murine Model of Alport's Syndrome," Meeting Abstract. Poster No. SU-P0347, American Society of Nephrology (ASN) 35th Annual Meeting & Scientific Exposition. Pennsylvania Convention Center: Philadelphia, PA. Nov. 1-3, 2002.

Dennis and Cosgrove, "Collagen XIII is induced on endothelial cells and may mediate VLA 1-dependent monocyte efflux in chronic renal fibrosis" Meeting Abstract. Abstract #329.39. FASEB Meeting on Experimental Biology: Translating the Genome 2004 Conference: Washington, DC. Apr. 17-21, 2004.

Fields et al., "Chapter 3: Principles and Practice of Solid-Phase Peptide Synthesis," in *Synthetic Peptides: A User's Guide*. Grant (ed.). W.M. Freeman & Company, New York, NY:1992. Title page, publishers page and pp. 77-183.

Gardner et al., "Deletion of integrin $\alpha1$ by homologous recombination permits normal murine development but gives rise to a specific deficit in cell adhesion," 1996. *Developmental Biology* 175:301-313.

Gowen et al., "The collagenous domain of class A scavenger receptors is involved in macrophage adhesion to collagens," Apr. 2001. *Journal of Leukocyte Biology* 69:575-582.

Gullberg et al., "Collagen-binding I domain integrins—what do they do?" 2002. *Programs in Histochemistry and Cytochemistry* 37(1):10-54.

Hägg et al., "Type XIII collagen: a novel cell adhesion component present in a range of cell-matrix adhesions and in the intercalated discs between cardiac muscle cells," 2001. *Matrix Biology* 19:727-742.

Hägg et al., "Type XIII collagen is identified as a plasma membrane protein," Jun. 19, 1998. *The Journal of Biological Chemistry* 273(25):15590-15597.

Harlan and Winn, "Leukocyte-endothelial interactions: clinical trials of anti-adhesion therapy," 2002. *Critical Care Medicine* 30(5 Suppl.): S214-S219.

Harlow et al., *Antibodies: A Laboratory Manual*, Cold Spring Harbor Laboratory Press, Cold Spring Harbor, NY; 1988. Title page, publisher's page, and pp. 141-155.

Heeringa et al., "Renal expression of endothelial and inducible nitric oxide synthase, and formation of peroxynitrite-modified proteins and reactive oxygen species in Wegener's granulomatosis," 2001. *Journal of Pathology* 193:224-232. Published online Dec. 7, 2000.

Huang, "Structural chemistry and therapeutic intervention of protein-protein interactions in immune response, human immunodeficiency virus entry, and apoptosis," Jun. 2000 *Pharmacology & Therapeutics* 86(3):201-215.

Ianaro et al., "Anti-very late antigen-1 monoclonal antibody modulates the development of secondary lesion and T-cell response in experimental arthritis," Jan. 2000. *Lab Invest.* 80(1):73-80.

Kagami et al., "Effects of anti-$\alpha1$ integrin subunit antibody on anti-Thy-1 glomerulonephritis," 2002. *Laboratory Investigation* 82(9):1219-1224.

Kim, "Cytokines and adhesion molecules in stroke and related diseases," 1996. *Journal of the Neurological Sciences* 137:69-78.

Kosswig et al., "Class A scavenger receptor-mediated adhesion and internalization require distinct cytoplasmic domains," Sep. 5, 2003. *The Journal of Biological Chemistry* 278(36):34219-34225. Published online Jun. 20, 2003.

Krieglstein et al., "Collagen-binging integrin $\alpha1\beta1$ regulates intestinal inflammation in experimental colitis," Dec. 2002 *The Journal of Clinical Investigation* 110(12):1773-1782.

Kvist et al., "Lack of cytosolic and transmembrane domains of type XIII collagen results in progressive myopathy," Oct. 2001. *American Journal of Pathology* 159(4):1581-1592.

Laakkonen et al., "A tumor-homing peptide with a targeting specificity related to lymphatic vessels," Jul. 2002. *Nature Medicine* 8(7):751-755. Published online Jun. 10, 2002.

Lalor et al., "Vascular adhesion protein-1 mediates adhesion and transmigration of lymphocytes on human hepatic endothelial cells," 2002 *The Journal of Immunology* 169:983-992.

Lin et al., "Induced repatterning of type XVIII collagen expression in ureter bud from kidney to lung type: association with sonic hedgehog and ectopic surfactant protein C," May 2001 *Development* 128(9):1573-1585.

Luby-Phelps, "Preparation of fluorescently labeled dextrans and ficolls," in *Methods in Cell Biology* vol. 29, Chapter 4: pp. 59-73. Academic Press; 1989.

Lund et al., "In vivo modifications of the maize mitochondrial small heat stress protein HSP22," Aug. 10, 2001. *The Journal of Biological Chemistry* 276(32):29924-29929. Published online Jun. 7, 2001.

Mendrick et al., "Glomerular epithelial and mesangial cells differentially modulate the binding specificities of VLA-1 and VLA-2," Mar. 1995. *Laboratory Investigation* 72(3):367-375.

Metzler et al., "Solution structure of human CTLA-4 and delineation of a CD80/CD86 binding site conserved in CD28," Jul. 1997. *Nature Structural Biology* 4(7):527-531.

Mountain, "Gene therapy: the first decade," Mar. 2000. *Trends in Biotechnology* 18(3):119-128.

Nykvist et al., "Distinct recognition of collagen subtypes by $\alpha1\beta1$ and $\alpha2\beta1$ integrins. $\alpha1\beta1$ mediates cell adhesion to type XIII collagen," Mar. 17, 2000. *The Journal of Biological Chemistry* 275(11):8255-8261.

Pihlajaniemi and Tamminen, "The $\alpha1$ chain of type XIII collagen consists of three collagenous and four non-collagenous domains, and its primary transcript undergoes complex alternative splicing," Oct. 5, 1990. *The Journal of Biological Chemistry* 265(28):16922-16928.

Rodgers et al., "Monocytes may promote myofibroblast accumulation and apoptosis in Alport renal fibrosis," 2003. *Kidney International* 63:1338-1355.

Roebuck, "Oxidant stress regulation of IL-8 and ICAM-1 expression: Differential activation and binding of transcription factors AP-1 and NF-$\kappa$B," 1999. *International Journal of Molecular Medicine* 4:223-230.

Rouslahti, "Targeting tumor vasculature with homing peptides from phage display," 2000. *Seminars in Cancer Biology* 10:435-442.

Sampson et al., "Global gene expression analysis reveals a role for the α1 integrin in renal pathogenesis," Sep. 7, 2001. *The Journal of Biological Chemistry* 276(36):34182-34188. Published online Jul. 10, 2001.

Snellman et al., "Type XIII collagen forms monotrimers with three helical collagenaous domains and its association into disulfide-bonded trimers is enhanced by prolyl-4-hyroxylase," Mar. 24, 2000. *The Journal of Biological Chemistry* 275(12):8936-8944.

Tu et al., "The type XIII collagen ectodomain is a 150-nm rod and capable of binding to fibronectic, nidogen-2, perlecan, and heparin," Jun. 21, 2002. *The Journal of Biological Chemistry* 277(25):23092-23099.

Yoon et al., "Sustained production of $H_2O_2$ activates pro-matrix metalloproteinase-2 through receptor tyrosine kinases/phosphatidylinositol 3-kinase/NF-κB pathway," Aug. 16, 2002. *The Journal of Biological Chemistry* 277(33):30271-30282. Published online Jun. 10, 2002.

Yusuf-Makagiansar et al., "Inhibition of LFA-1/ICAM-1 and VLA-4/VCAM-1 as a therapeutic approach to inflammation and autoimmune diseases," 2002 *Medicinal Research Reviews* 22(2):146-167.

* cited by examiner

Anti-CD11b | Anti-α1β1 integrin

A. B.

CD11b

Alexa Dex

VLA1

Alexa Dex

A

B

```
                         SEQUENCE LISTING

<160> NUMBER OF SEQ ID NOS: 10

<210> SEQ ID NO 1
<211> LENGTH: 8
<212> TYPE: PRT
<213> ORGANISM: artificial sequence
<220> FEATURE:
<223> OTHER INFORMATION: artificially synthesized peptide

<400> SEQUENCE: 1

Gly Ala Glu Gly Ser Pro Gly Leu
1               5

<210> SEQ ID NO 2
<211> LENGTH: 12
<212> TYPE: PRT
<213> ORGANISM: artificial sequence
<220> FEATURE:
<223> OTHER INFORMATION: artificially synthesized peptide

<400> SEQUENCE: 2

Gly Glu Lys Gly Ala Glu Gly Ser Pro Gly Leu Leu
1               5                   10

<210> SEQ ID NO 3
<211> LENGTH: 20
<212> TYPE: DNA
<213> ORGANISM: artificial sequence
<220> FEATURE:
<223> OTHER INFORMATION: oligonucleotide primer

<400> SEQUENCE: 3
ggagctgtcg tattccagtc                                              20

<210> SEQ ID NO 4
<211> LENGTH: 20
<212> TYPE: DNA
<213> ORGANISM: artificial sequence
<220> FEATURE:
<223> OTHER INFORMATION: oligonucleotide primer

<400> SEQUENCE: 4
aacccctcaa gacccgttta                                              20
```

```
<210> SEQ ID NO 5
<211> LENGTH: 30
<212> TYPE: DNA
<213> ORGANISM: artificial sequence
<220> FEATURE:
<223> OTHER INFORMATION: oligonucleotide primer

<400> SEQUENCE: 5
ggtgaaggtc ggagtcaacg gatttggtcg                                          30

<210> SEQ ID NO 6
<211> LENGTH: 29
<212> TYPE: DNA
<213> ORGANISM: artificial sequence
<220> FEATURE:
<223> OTHER INFORMATION: oligonucleotide primer

<400> SEQUENCE: 6
ggatctcgct cctggaagat ggtgatggg                                           29

<210> SEQ ID NO 7
<211> LENGTH: 20
<212> TYPE: DNA
<213> ORGANISM: artificial sequence
<220> FEATURE:
<223> OTHER INFORMATION: oligonucleotide primer

<400> SEQUENCE: 7
gagcggggca tgccaggaat                                                     20

<210> SEQ ID NO 8
<211> LENGTH: 20
<212> TYPE: DNA
<213> ORGANISM: artificial sequence
<220> FEATURE:
<223> OTHER INFORMATION: oligonucleotide primer

<400> SEQUENCE: 8
tggccatcaa caccagcttc                                                     20

<210> SEQ ID NO 9
<211> LENGTH: 24
<212> TYPE: DNA
<213> ORGANISM: artificial sequence
<220> FEATURE:
<223> OTHER INFORMATION: oligonucleotide primer

<400> SEQUENCE: 9
ctgcgctcca acccgataat gtcc                                                24

<210> SEQ ID NO 10
<211> LENGTH: 22
<212> TYPE: DNA
<213> ORGANISM: artificial sequence
<220> FEATURE:
<223> OTHER INFORMATION: oligonucleotide primer

<400> SEQUENCE: 10
tgggggcctg cttgtcctgt ct                                                  22
```

INDUCIBLE LIGAND FOR α1β1 INTEGRIN AND USES

CONTINUING APPLICATION DATA

This application is a divisional patent application of U.S. patent application Ser. No. 10/698,121 filed on Oct. 31, 2003, now U.S. Pat. No. 7,348,002 which claims the benefit of U.S. Provisional Application Ser. No. 60/423,297, filed Nov. 1, 2002, both of which are incorporated herein by reference in their entirety.

GOVERNMENT FUNDING

The present invention was made with government support under Grant No. R01DK55000, awarded by the National Institutes of Health. The Government has certain rights in the invention.

BACKGROUND

A specific integrin receptor, integrin α1β1, plays a role in the progression of interstitial disease associated with Alport syndrome. This effect was illustrated by crossing the Alport mouse with a knockout mouse for the integrin α1 gene (Cosgrove et al., Am. J. Path., 157, 1649-1659 (2000)). The integrin knockout mutation has no obvious effect on renal development or function in normal mice, even though it is widely expressed in the kidney (Gardner et al., Dev. Biol. 175, 301-313 (1996)). When the α1 integrin mutation was added to the genetic background of the Alport mouse, however, both glomerular and tubulointerstitial disease were markedly attenuated. Attenuation of the glomerular pathogenesis was linked to the effect on mesangial expansion and the deposition of mesangial laminins in the GBM (Cosgrove et al., Am. J. Path., 157, 1649-1659 (2000)). The effect of the α1 integrin null mutation on tubulointerstitial disease, however, was less clear.

SUMMARY

The present invention is based on the discovery of the presence of a specific inducible ligand on the vascular endothelial cell surface of Alport mouse kidneys. Significantly, this provides for a wide variety of therapeutic methods and for methods of identifying compounds (e.g., small organic molecules and peptides) suitable for use in such therapeutic methods.

Preferably, the specific inducible ligand is present on the vascular endothelial cell surface of Alport mouse kidneys, but not normal kidneys. The ligand binds to purified integrin α1β1, and monocytes in Alport kidneys are integrin α1β1-positive. Newly effluxed monocytes, based on monocyte trafficking assays, are integrin α1β1-positive, while only a fraction of the bone marrow-derived monocytes (10%) are integrin α1β1-positive. The rate of monocyte efflux in integrin α1β1-deficient Alport (DKO) mice is much slower than that no Alport mice. Functionally blocking the ligand by injection with purified integrin α1β1 (purchased from Chemicon, Temecula, Calif.) reduces the rate of monocyte efflux into the interstitial space of Alport kidneys. Combined, this evidence proves the existence of an inducible ligand for integrin α1β1 on Alport vascular endothelium, which mediates selective efflux of integrin α1β1-positive monocytes into the interstitium. The DKO data showing delayed onset of efflux with a much slower rate of efflux, combined with the ligand blocking data by injection of purified α1β1 integrin, illustrate that functionally blocking this ligand (defined as the substance in the kidneys that binds Alexa-labeled integrin α1β1, within 6 hours of injecting this reagent into the tail vein of a 7 week old Alport mouse in a pure 129 Sv/J genetic background) will reduce the rate of monocyte efflux, which would be therapeutically beneficial for any chronic inflammatory disease where integrin α1β1-positive interstitial monocyte/lymphocyte accumulation is observed.

In one embodiment, the present invention provides a method of treating a patient having a chronic inflammatory disease. The method includes administering to the patient a blocking agent (e.g., a peptide or a neutralizing antibody) to neutralize the capacity of Collagen XIII to bind to a α1β1 integrin. The chronic inflammatory disease is preferably characterized by progressive pathogenesis resulting from infiltrating monocytes, lymphocytes, or both. Examples of such chronic inflammatory diseases include renal fibrosis, lung fibrosis, liver fibrosis, rheumatoid arthritis, psoriasis, experimental colitis, or crescentic glomerulonephritis. Preferably, the blocking agent blocks the interaction of α1β1 integrin on peripheral blood monocytes and/or lymphocytes with Collagen XIII on vascular endothelium of chronically inflamed tissues.

In another embodiment, the present invention provides a method for treating a subject having an inflammatory disease or other condition where integrin α1β1-positive interstitial monocyte and/or lymphocyte accumulation is observed. The method involves administering to the subject an active agent that disrupts the interaction between Collagen XIII and α1β1 integrin. Preferably, the active agent blocks binding of Collagen XIII (on vascular endothelium of chronically inflamed tissues) and α1β1 integrin (on peripheral blood monocytes and/or lymphocytes). Preferably, the blocking agent is a peptide or an antibody. Preferably, the inflammatory disease or other condition is renal fibrosis, lung fibrosis, liver fibrosis, rheumatoid arthritis, psoriasis, experimental colitis, or crescentic glomerulonephritis.

In another embodiment, the present invention provides a method of reducing selective efflux of integrin α1β1-positive monocytes into the interstitium of chronically inflamed tissues. The method involves contacting the α1β1 integrin on peripheral blood monocytes and/or lymphocytes with an active agent that interferes with the interaction between Collagen XIII and α1β1 integrin. This can be accomplished in several different ways. For example, reducing selective efflux of integrin α1β1-positive monocytes into the interstitium of chronically inflamed tissues involves contacting the α1β1 integrin with a peptide having at least a portion of the amino acid sequence of Collagen XIII that binds specifically to α1β1 integrin. Alternatively, reducing selective efflux of integrin α1β1-positive monocytes into the interstitium of chronically inflamed tissues involves contacting an antibody that binds to the Collagen XIII ligand on the cell surface of the vascular/capillary endothelial cells of inflamed tissues under conditions effective to block the binding site for Collagen XIII. In yet another alternative embodiment, reducing selective efflux of integrin α1β1-positive monocytes into the interstitium of chronically inflamed tissues involves contacting the vascular endothelium with small inhibitory RNAs under conditions effective to prevent the expression of Collagen XIII protein on the cell surface.

In another embodiment, the present invention provides a method of reducing the rate of monocyte and/or lymphocyte efflux into the interstitial space of chronically inflamed tissues. The method involves blocking Collagen XIII from binding with α1β1 integrin. This can occur by blocking the Collagen XIII ligand or it can occur by blocking α1β1 integrin. In one embodiment, the blocking agent is a peptide fragment of Collagen XIII containing the binding site for α1β1 integrin. In an alternative embodiment, the blocking agent is a monospecific antibody that binds Collagen XIII on the vascular/capillary endothelial cell surface of inflamed tissues.

In yet another embodiment, the present invention provides a method of reducing the rate of monocyte and/or lymphocyte efflux into the interstitial space of chronically inflamed tissues. The method involves blocking Collagen XIII from binding with α1β1 integrin.

In another embodiment, the present invention provides a method of blocking the interaction of α1β1 integrin on peripheral blood monocytes and/or lymphocytes with Collagen XIII on vascular endothelium of chronically inflamed tissues. The method involves contacting the monocytes and/or lymphocytes, the vascular endothelium, or both with an agent that either occupies the Collagen XIII binding site on α1β1 integrin (e.g., a peptide inhibitor) or blocks the α1β1 binding site on Collagen XIII (e.g., a neutralizing monoclonal antibody).

The present invention provides a method of identifying an agent that inhibits the efflux of monocytes into the interstitial space of a model where interstitial monocytes or lymphocytes are implicated. The method involves identifying an agent that disrupts the interaction between Collagen XIII and α1β1 integrin. In one embodiment, the agent inhibits binding of Alexa-conjugated purified α1β1 integrin to MCP-1 treated primary endothelial cells. In an alternative embodiment, the agent is an antibody that blocks the interaction of Alexa-conjugated purified α1β1 integrin to MCP-1-treated vascular endothelial cells in culture.

The present invention also provides an isolated peptide having the sequence GAEGSPGL (SEQ ID NO. 1), wherein the peptide disrupts (e.g., blocks) the interaction between Collagen XIII and α1β1 integrin. Preferably, the isolated peptide has the sequence GEKGAEGSPGLL (SEQ ID NO:2). In certain embodiments, the isolated peptide is 8-16 amino acids in length. In other embodiments, the isolated peptide is 12-16 amino acids in length. For certain embodiments, the isolated peptide consists of GAEGSPGL (SEQ ID NO. 1). For certain embodiments, the isolated peptide consists of GEKGAEGSPGLL (SEQ ID NO:2).

The present invention also provides an isolated peptide having an amino acid sequence that has at least 70% sequence identity to GAEGSPGL (SEQ ID NO. 1), wherein the peptide disrupts the interaction between Collagen XIII and α1β1 integrin. In another embodiment, the present invention provides an isolated peptide having an amino acid sequence that has at least 70% sequence identity to GEKGAEGSPGLL (SEQ ID NO:2), wherein the peptide disrupts the interaction between Collagen XIII and α1β1 integrin.

The present invention also provides antibodies to the peptides described herein.

As used herein, "a" or "an" means one or more (or at least one), such that combinations of active agents (i.e., active oxidative stress regulators), for example, can be used in the compositions and methods of the invention. Thus, a composition that includes "a" polypeptide refers to a composition that includes one or more polypeptides.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE DRAWINGS

FIGS. 3B and 3D show the Alexa568-positive cells in the interstitium of Alport kidneys 3 days following tail vein injection of Alexa 568-conjugated dextrans. Only monocytes (CD11b is a specific marker for monocytes) are labeled (all fluorescent signals in FIG. 3B line up with fluorescent signals in FIG. 3A). Newly effluxed monocytes (FIG. 3D) are all immuno-positive for integrin a1b1 (VLA1, FIG. 3C).

FIG. 4A. Monocyte trafficking assessed via tail vein injection of Alexa 568-labelled dextrans was analyzed in Alport mice relative to α1β1-integrin-deficient (DKO) Alport mice as a function of renal disease development. Data points represent twenty fields (at 200× magnification) for two independent animals. Only CD11b-positive/Alexa-positive signals were scored, using Image Pro-Plus (Media Cybernetics, Bethesda, Md.) software. The clearly data indicate that the onset of monocyte efflux is delayed in DKO mice relative to Alport mice. The slopes of the curves (derived from linear regression using Sigma Plot (Sigma, St. Louis, Mo.) software) indicate that the rate of monocyte efflux in DKO mice is markedly lower than that for Alport mice. FIG. 4B. Alport mice were either injected or not with 5 μg of purified α1β1 integrin one day before injection with labeled dextrans, and boosted with 5 μg each day until three days following labeled dextran injection. Cryosections were stained for monocytes (anti-cd11b) and dual labeled cells counted as above. Results indicate a reduction in monocyte efflux in mice injected with the purified integrin, defining that the functions to mediate efflux monocytes into the tubulointerstitial space. Bars represent standard error.

FIG. 5C shows that Alexa-labeled integrin binding is not phagocytized integrin in monocytes, since the two signals (compare the location of signal in FIG. 5B with signal in FIG. 5C) do not co-localize.

DETAILED DESCRIPTION OF ILLUSTRATIVE EMBODIMENTS OF THE INVENTION

Figure 1:
FIGS. 1A and 1B. Monocytes in Alport interstitium are predominantly integrin α1β1-positive. Panels show immunofluorescence immunostaining of tissue sections from Alport renal cortex at indicated ages using antibodies against CD11b (FIG. 1A) and integrin α1β1 (FIG. 1B). Note that all monocytes are immunopositive for α1β1 integrin.
Figure 1:

The present invention is based on the discovery of the presence of a specific inducible ligand on the vascular endothelial cell surface of Alport mouse kidneys. Significantly, this provides for a wide variety of therapeutic methods aimed at disrupting the interaction between the inducible ligand and its receptor (α1β1 integrin).

The specific inducible ligand is Collagen XIII. Collagen XIII mRNA is induced in endothelial cells from Alport kidneys relative to controls. The binding of purified α1β1 integrin is induced by MCP-1 and hydrogen peroxide. Labeled α1β1 integrin injected into the tail vein of Alport mice, but not normal mice, binds to the vascular endothelium. It should be noted, however, that basal levels of Collagen XIII expression are observed on vascular endothelium of normal mice and untreated endothelial cell cultures. It is likely that other factors contribute to the "inducible" binding. Likely candidates are the selectins, which are a family of proteins that promote "slow rolling" of lymphocytes, monocytes, and b-cells on the vascular endothelium. This slow rolling is required to promote firm adhesion via more classical ligand/receptor interactions. The selectins are induced on the vascular endothelium of inflammatory tissues, but not normal tissues.

Significantly, the present invention provides methods for treating inflammatory diseases or other conditions where integrin α1β1-positive interstitial monocyte and/or lymphocyte accumulation is observed. Such methods involve administering to a subject afflicted with such a condition an active agent that disrupts (e.g., blocks or otherwise neutralizes) the interaction between the inducible ligand Collagen XIII and its receptor α1β1 integrin. Such conditions include, for example, renal fibrosis, lung fibrosis, liver fibrosis, rheumatoid arthritis, psoriasis, experimental colitis, and crescentic glomerulonephritis. The present invention also provides methods of identifying agents (e.g., small organic molecules, peptides, antibodies, SiRNAs) suitable for use in such therapeutic methods.

Specifically, the following discoveries are presented herein: the inducible ligand binds to purified integrin α1β1; all monocytes in Alport kidneys are integrin α1β1-positive; newly effluxed monocytes, based on monocyte trafficking assays, are all integrin α1β1-positive, while only a fraction of the bone marrow-derived monocytes (10%) are integrin α1β1-positive; the rate of monocyte efflux in integrin α1β1-deficient Alport (DKO) mice is much slower than that no Alport mice; and functionally blocking the ligand by injection with purified integrin α1β1 reduces the rate of monocyte efflux into the interstitial space of Alport kidneys. Combined, this evidence proves the existence of an inducible ligand for integrin α1β1 on Alport vascular endothelium, which mediates selective efflux of integrin α1β1-positive monocytes into the interstitium.

Thus, the present invention provides a method of blocking/reducing selective efflux of integrin α1β1-positive monocytes into the interstitium of chronically inflamed tissues. This method involves contacting the α1β1 integrin on circulating peripheral blood monocytes/lymphocytes with an active agent described herein (e.g., a peptide with the composition of the portion of Collagen XIII that binds specifically to α1β1 integrin). Alternatively, this method involves the administration of an active agent (e.g., a humanized monospecific antibody preparation) that will bind to the Collagen XIII ligand on the cell surface of the vascular/capillary endothelial cells of inflamed tissues in such a way that the bound active agent (e.g., antibody) blocks the binding site for Collagen XIII, thus preventing the binding of α1β1 integrin on the peripheral blood monocytes/lymphocytes with the Collagen XIII on the vascular/capillary endothelial cells. Further, this method can involve the use of active agents (e.g., small inhibitory RNAs) that are targeted to the vascular endothelium in such a way as to prevent the expression of Collagen XIII protein on the cell surface, thus preventing/reducing the adhesion/transendothelial migration of α1β1 integrin-positive monocytes/lymphocytes into inflamed tissues.

The DKO data showing delayed onset of efflux with a much slower rate of efflux, combined with the ligand blocking data by injection of purified α1β1 integrin, illustrate that functionally blocking this ligand (defined as the substance in the kidneys that binds Alexa-labeled integrin α1β1 within 6 hours of injecting this reagent into the tail vein of a 7 week old Alport mouse in a pure 129 Sv/J genetic background) will reduce the rate of monocyte efflux.

Thus, the present invention provides a method of reducing the rate of monocyte (and/or lymphocyte) efflux into the interstitial space of chronically inflamed tissues. This method involves blocking Collagen XIII from binding with α1β1 integrin, especially as the α1β1 integrin receptor is presented to the Collagen XIII ligand on the surface of circulating peripheral blood monocytes or lymphocytes, by contacting the α1β1 integrin on the cell surface of lymphocytes and/or monocytes with an agent that disrupts (e.g., blocks or otherwise neutralizes) the interaction between Collagen XIII and α1β1 integrin. This can result from the use of an active agent such as apeptide fragment of Collagen XIII containing the binding site for α1β1 integrin, for example. Alternatively, this method can involve the use of an active agent, such as a mono-specific antibody, that binds Collagen XIII on the vascular/capillary endothelial cell surface of inflamed tissues in such a way as to block the ability of Collagen XIII on the vascular endothelial cells from interacting (e.g., binding) with α1β1 integrin on the circulating peripheral blood monocytes/lymphocytes, thus preventing/reducing adhesion and transmigration of integrin α1β1-positive lymphocytes/monocytes into the interstitial spaces of the inflamed tissues.

Bone marrow transfer studies with Alexa-568 dextran-loaded monocytes showed a significant decrease in the rate of monocyte efflux for cells derived from α1 integrin null mice compared to controls. Using a phage display approach for detecting interacting binding partners, Collagen XIII was identified as the endothelial cell ligand for α1β1 integrin. This unique membrane bound collagen has been previously shown to bind α1β1 integrin, but its function prior to the findings documented herein, was unknown. Elevated expression of Collagen XIII occurs on endothelial cells from Alport mice relative to controls. Collagen XIII is induced in kidney endothelial cell cultures by monocyte chemo-attractive protein 1 (MCP-1), a chemokine previously documented as induced in Alport kidneys, and well characterized for its role in monocyte recruitment in chronically inflamed tissues. Blocking the ability of Collagen XIII to bind to α1β1 integrin will be therapeutically beneficial for any chronic inflammatory disease where integrin α1β1-positive interstitial monocyte accumulation is observed. Thus, the present invention provides a method of treating a chronic inflammatory disease, such as renal fibrosis, lung fibrosis, liver fibrosis, rheumatoid arthritis, psoriasis, experimental colitis, and crescentic glomerulonephritis. The method involves blocking binding (or otherwise neutralizing the interaction) of Collagen XIII to α1β1 integrin. In this context, "treating" means that there is improvement in at least one clinical symptom of the condition. For example, treating can involve slowing or arresting the progression of a chronic inflammatory condition by inhibiting or reducing the efflux of monocytes/lymphocytes into the interstitial spaces of the site(s) of chronic inflammation.

Using the Alexa-conjugated dextran injection approach described herein, one skilled in the art could assay for a therapeutic agent (i.e., an active agent) for its ability to inhibit the efflux of monocytes into the interstitial space of a model (e.g., a mouse model) where interstitial monocytes or lymphocytes are implicated. In this context, "inhibit" means to arrest or reduce the rate transendothelial migration of lymphocytes/monocytes from the peripheral blood circulation into the interstitial spaces of the inflamed tissues by blocking or reducing the adhesion of the α1β1 integrin receptor on the peripheral blood lymphocyte/monocyte cell surface to the Collagen XIII ligand on the vascular/capillary endothelium of the inflamed tissue.

Such assays include, for example, at least two experimental strategies. The first assay includes an analysis of the capacity of the therapeutic agent in question to inhibit binding of Alexa-conjugated purified α1β1 integrin to MCP-1 treated primary endothelial cells. This can be done, for example, using a 96-well microtiter plate format and a fluorescence plate reader as described in the specific methods. Formulations can be titrated into the binding assay, and their relative efficacy judged by the concentration required to inhibit binding. Peptides, antibodies, or SiRNAs can then be introduced into the Alport mouse model at various doses. Efficacy in vivo can be quantitatively assessed by injection of Alexa fluorochrome-conjugated dextrans according to the specific methods described herein. Labeled cells in the interstitium are all monocytes (for example, see FIGS. 3A and 3B). The percentage (%) decrease in the number of Alexa-labeled monocytes compared to age and sex matched vehicle-injected Alport mice can be considered a direct measure of the efficacy in vivo for the particular agent in question.

The second assay involves the use of mono-specific antibodies. These antibodies are raised by injecting the peptide antigen comprising the integrin binding domain of Collagen XIII (e.g., SEQ ID NO: 2) into mice or into rats so as to elicit an immuno response to the peptide antigen. Antibody-producing B-cells from these animals are isolated from the spleen and fused to myeloma cells using conventional techniques (polyethylene glycol fusion method). The culture supernatant from clonal populations of antibody producing cells (hybridomas) contains the mono-specific (or monoclonal) antibody. Antibodies prepared in this way are assayed first for their ability to block the interaction of Alexa-conjugated purified α1β1 integrin to MCP-1-treated vascular endothelial cells in culture as described herein. Mono-specific antibodies that have this property will be assayed in vivo.

The antibody is purified from the culture supernatant by binding to, and then eluting from protein-A sepharose, which is a standardized procedure for the purification/concentration of antibodies from hybridoma supernatants. An effective amount of the antibody will be injected into the Alport mouse model and 24 hours later the same mouse will be injected with Alexa-conjugated dextrans. Three days following the injection of dextrans, the kidneys will be harvested, and cryosections counterstained with FITC-conjugated anti-CD11b antibodies (to label the monocytes), and the Alexa-positive monocytes counted. The number of Alexa-positive monocytes is compared with that for age and sex matched Alport mice given an equivalent dose of an isotype-matched irrelevant antibody. A significant reduction in Alexa-positive (newly effluxed) monocytes indicates an antibody with potential therapeutic benefits. Such therapeutic agents include, but are not limited to, small organic molecules, isolated peptides having the sequence GAEGSPGL (SEQ ID NO. 1), or more particularly, GEKGAEGSPGLL (SEQ ID NO:2), antibodies to such peptides, and small inhibitory RNAs (SiRNAs). Herein, an "isolated" peptide is one that is naturally occurring or synthetically derived and is not in its natural environment.

Preferably, the isolated peptides can have at least 8 amino acids. More preferably, they have at least 12 amino acids. The length of the peptides is sufficient to obtain the desired function. For certain embodiments, they are no larger than 16 amino acids in length.

This sequence of amino acids on Collagen XIII on the vascular endothelium interacts with the α1β1 integrin on circulating white blood cells. Additionally, active peptides (i.e., active analogs of SEQ ID NOs: 1 or 2) can include those having a sequence that has at least 70% sequence identity to GAEGSPGL (SEQ ID NO. 1), or more particularly, GEKGAEGSPGLL (SEQ ID NO:2). Preferably, an active analog has a structural similarity to one of SEQ ID NOs:1 or 2 of at least 80% identity, more preferably, at least 90% identity, and even more preferably, at least 95% identity. Such peptides do not include Collagen XIII.

Neutralizing antibodies made against at least one of these peptides or against α1β1 integrin can also be used to disrupt the capacity of Collagen XIII to bind to α1β1 integrin. Small inhibitory RNAs (SiRNAs) delivered to the endothelial cells resulting in the intracellular destruction of Collagen XIII transcripts, and thus preventing translated Collagen XIII protein from reaching the endothelial cell surface, can also be used.

These agents can be used alone or together to partially or wholly inhibit the transendothelial migration of integrin α1β1-positive monocytes/lymphocytes into the interstitial space of chronically inflamed tissues.

Such inhibitors are referred to herein as "active agents." Significantly, such active agents can be administered alone or in various combinations to a patient (e.g., animals including humans) as a medication or dietary (e.g., nutrient) supplement in a dose sufficient to produce the desired effect throughout the patient's body, in a specific tissue site, or in a collection of tissues (organs).

The polypeptides described herein (e.g., those that include the amino acids of SEQ ID NO:1 or SEQ ID NO:2) can be in their free acid form or they can be amidated at the C-terminal carboxylate group.

As discussed above, the present invention also includes analogs of the polypeptides of SEQ ID NO:1 and SEQ ID NO:2, which include polypeptides having structural similarity. These peptides can also form a part of a larger peptide. An "analog" of a polypeptide includes at least a portion of the polypeptide, wherein the portion contains deletions or additions of one or more contiguous or noncontiguous amino acids, or containing one or more amino acid substitutions. An "analog" can thus include additional amino acids at one or both of the termini of the polypeptides listed above. Substitutes for an amino acid in the polypeptides of the invention are preferably conservative substitutions, which are selected from other members of the class to which the amino acid belongs. For example, it is well known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

As stated above, active analogs include polypeptides having structural similarity (i.e., sequence identity). Structural similarity is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the NCBI BLASTB, version 2.2.6, of the BLAST 2 search algorithm. Preferably, the default values for all BLAST 2 search parameters are used with slight variations for Protein: Search for Short Nearly Exact Matches available at http://www.ncbi.nlm.nih.gov/BLAST/Blast.cgi?CMD=Web&LAYOUT=Two Windows&AUTO_FORMAT=Semiauto&ALIGNMENTS=50&ALIGNMENT_VIEW=Pairwise&CLIENT=web&DATABASE=nr&DESCRIPTIONS=100&ENTREZ_QUERY=%28none%29& EXPECT=20000&FORMAT_OBJECT=Alignment&FORMAT_TYPE=HTML&GAPCOSTS=9+1&I_THRESH=0.005&MATRIX_NAME=PAM30&NCBI_GI=on&PAGE=Proteins&PROGRAM=blastp&SERVICE=plain&SET_DEFAULTS.x=24&SET_DEFAULTS.y=10&SHOW_OVERVIEW=on&WORD_SIZE=2&END_OF_HTTPGET=Yes&SHOW_LINKOUT=yes&GET_SEQUENCE=yes including matrix=PAM30; open gap penalty=10, extension gap penalty=1, expect=20000, word-size=3, and filter on=low complexity. In the comparison of two amino acid sequences using the BLAST search algorithm, structural similarity is referred to as "identity."

Such peptide inhibitors can be derived (preferably, isolated and purified) naturally such as by phage display or yeast two-hybrid methods for identifying interacting proteins, or they can be synthetically constructed using known peptide polymerization techniques. Whether naturally occurring or synthetically constructed, such peptides are referred to herein as "isolated." For example, the peptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W.M. Freeman & Company, New York, N.Y., pp. 77-183 (1992).

The peptides used in the methods of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary, but from about 4 to 8 peptides per carrier molecule are typically obtained under standard coupling conditions.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-carbodiimide hydrochloride (EDC; ten times the amount of peptide) is dissolved in a small amount of water. The EDC solution was added to the peptide/ovalbumin mixture and allowed to react for a number of hours. The mixture may then dialyzed (e.g., into phosphate buffered saline) to obtain a purified solution of peptide/ovalbumin conjugate. Peptide/carrier molecule conjugates prepared by this method typically contain about 4 to 5 peptides per ovalbumin molecule.

The invention further provides to an antibody capable of specifically binding to a peptide having at least a 70% (more preferably, at least 80%, even more preferably, at least 90%, and even more preferably, at least 95%) sequence identity to a peptide that includes the amino acids of SEQ ID NO:1 or SEQ ID N:2. In one embodiment, the antibody is a monoclonal antibody and in another embodiment, the antibody is a polyclonal antibody. In another embodiment the antibody is an antibody fragment, which is included in the use of the term antibody. The antibody can be obtained from a mouse, a rat, a human or a rabbit. Methods for preparing antibodies to peptides are well known to one of skill in the art. In a preferred example, the antibodies can be human derived, rat derived, mouse derived, or rabbit derived. Protein-binding antibody fragments and chimeric fragments are also known and are within the scope of this invention.

The present invention also provides a composition that includes one or more active agents of the invention and one or more carriers, preferably a pharmaceutically acceptable carrier. The methods of the invention include administering to, or applying to the skin of, a patient (i.e., a subject), preferably a mammal, and more preferably a human, a composition of the invention in an amount effective to produce the desired effect. The active agents of the present invention are formulated for internal administration (oral, rectal, etc.) or parenteral administration (injection, internal pump, etc.). The administration can be via direct injection into tissue, interarterial injection, intravenous injection, or other internal administration procedures, such as through the use of an implanted pump, or via contacting the composition with a mucous membrane in a carrier designed to facilitate transmission of the composition across the mucous membrane such as a suppository, eye drops, inhaler, or other similar administration method or via oral administration in the form of a syrup, a liquid, a pill, capsule, gel coated tablet, or other similar oral administration method. The active agents can be incorporated into an adhesive plaster, a patch, a gum, and the like, or it can be encapsulated or incorporated into a bio-erodible matrix for controlled release.

The carriers for internal administration can be any carriers commonly used to facilitate the internal administration of compositions such as plasma, sterile saline solution, IV solutions or the like. Carriers for administration through mucous membranes can be any well-known in the art. Carriers for administration orally can be any carrier well-known in the art.

The formulations may be conveniently presented in unit dosage form and may be prepared by any of the methods well known in the art of pharmacy. All methods include the step of bringing the active agent into association with a carrier, which constitutes one or more accessory ingredients. In general, the formulations are prepared by uniformly and intimately bringing the active agent into association with a liquid carrier, a finely divided solid carrier, or both, and then, if necessary, shaping the product into the desired formulations.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. The amount of active agent is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations include the active agent dissolved or suspended in one or more media such as mineral oil, DMSO, polyhydroxy alcohols, or other bases used for topical pharmaceutical formulations.

Useful dosages of the active agents can be determined by comparing their in vitro activity and the in vivo activity in animal models. Methods for extrapolation of effective dosages in mice, and other animals, to humans are known in the art.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Objects and advantages of this invention are further illustrated by the following examples, but the particular materials and amounts thereof recited in these examples, as well as other conditions and details, should not be construed to unduly limit this invention.

EXAMPLES

Introduction

In order to gain insight into the mechanism underlying the role of integrin α1 in Alport interstitial disease, a global analysis of gene expression using the Affymetrix gene chip method was employed. These experiments are described in Sampson et al., J. Biol. Chem., 276, 34182-34188 (2001). Alport mice at 7 weeks of age were compared with 7 week old DKO (double knockout mice null at both integrin α1 and collagen α3(IV)). Genes that were up or down-regulated were sorted using the classification scheme of Adams et al., Nature, 377, 3-174 (1995), and clustered within categories using the GENE CLUSTER and TREEVIEW programs. Among the observations made, it was noted that a number of monocyte/macrophage-specific transcripts were observed in the Alport mouse. These included macrophage chemoattractive protein 1 (MCP-1), macrophage inducible protein (IP-10), macrophage colony stimulating factor (M-CSF), macrophage mannose receptor, and F4/80. All of these transcripts were elevated between 6 and 24-fold in the Alport mice relative to control littermates. In kidneys from 7-week-old DKO mice, expression for all of these genes was restored to wild type levels. These studies led us to conclude that the effect of integrin α1 on Alport tubulointerstitial disease might be mediated by tissue monocytes. Immunostaining with a monocyte specific marker (CD11b) confirmed these suspicions, as it was clear that there were very few monocytes in the DKO mice, while they are abundant in the interstitium of Alport mice (Sampson et al., J. Biol. Chem., 276, 34182-34188 (2001)). T-cells and B-cells are virtually absent in Alport renal fibrosis (Rodgers et al., Kidney Int., 63, 1338-1355 (2003)).

Blocking α1β1 integrin has been shown to attenuate the progression of other chronic inflammatory disease models, including rheumatoid arthritis, experimental colitis, and crescentic glomerulonephritis. It has been proposed that this influence might involve the inhibition of leukocyte migration into tissues; however, the mechanism driving this proposed influence has remained unclear. It has recently been shown that the monocytes are mediating cellular destruction associated with progressive inflammation of the kidney in the Alport mouse model (Rodgers et al., Kidney Int., 63, 1338-1355 (2003)) underscoring the importance of interstitial monocyte accumulation in the pathology associated with chronic inflammatory diseases.

Herein, it is shown that a small population of monocytes in the bone marrow expresses α1β1 integrin, and that monocytes in the tubulointerstitium of Alport mice are positive for α1β1 integrin. Monocyte trafficking assays were used to show markedly attenuated efflux of monocytes in α1β1-null Alport mice compared to Alport mice, an that virtually all newly effluxed monocytes in Alport mice express α1β1 integrin. Using Alexa-conjugated purified α1β1 integrin, it was demonstrated that the integrin binds the vascular endothelial cells of Alport mice, but not normal mice, and that injection of the purified integrin suppresses monocyte efflux. Further, labeled monocytes from normal mice transplanted into α1 integrin-null Alport mice efflux more efficiently into the cortical interstitial space than monocytes from integrin α1 null mice. Combined, these data strongly suggest the existence of an inducible ligand for α1β1 integrin on the vascular endothelium of the kidney, which mediates efflux of α1β1 integrin-positive monocytes into the vascular endothelium. Using an endothelial cell-derived phage display library combined with a "biopanning" approach, Collagen XIII was identified as the endothelial cell ligand for α1β1 integrin. Interaction of α1β1 integrin on monocytes mediates transmigration into the interstitial space in chronic inflammatory diseases. In earlier work, compelling evidence was provided that the monocytes are responsible for the tubulointerstitial damage associated with the fibrotic process (Rodgers et al., Kidney Int., 63, 1338-1355 (2003)). Thus, identification of the endothelial cell-specific ligand may provide a therapeutic target of significant importance. Blocking the ligand with a neutralizing antibody or peptide inhibitor might be applied alone or in combination with blocking α1β1 integrin on the peripheral blood monocytes. This strategy will have implications for other chronic inflammatory diseases.

Methods

Alexa 568 Dextran Complex Protocol

Fluorescent dextrans were prepared according to the methods described by Luby-Phelps (Methods in Cell Biology, Vol. 29, Chap. 4, pp 59-73, (1989)). Briefly, 1 mg of the fluorescent probe, Alexa 568 (Molecular Probes, Inc. Eugene, Oreg.) was combined with 39 mg of dextran (Mol. Wt. Approximately 144,000) in the presence of pyridine, dimethylsulfoxide (DMSO), and tin dilaurate (Sigma-Aldrich Co. St. Louis, Mo.). Labeled dextran was precipitated with 95% ethanol, dialyzed in glass-distilled water and lyophilized. The dried product was then stored in 500 micrograms (μg) aliquots at −20° C. in a dessicator, protected from light.

Male wild type 129SV and 129SVJ mice (4-12 weeks old) along with collagen IV α3 (−/−) (Alport: 5-8 weeks old) and collagen IV α3 (−/−)/integrin α1 (−/−) double knock out (DKO: 8-12 weeks old) mice were tail vein injected with 50 kg of Alexa 568 labeled dextran reconstituted in 100 microliters (μL) Hanks Balanced Salt Solution (pH 7.2). Three days post injection animals were given a lethal injection of averitin (0.55 grams per kilogram (g/kg) body weight; ip) followed by cardiac perfusion with ice cold PBS. Kidneys were removed and immersed in increasing concentrations of ice cold sucrose (30% max) then embedded in Tissue Tek OCT mounting medium (Sakura Finetek USA, Inc., Torrence, Calif.) and stored at −80° C.

Fresh frozen tissue sections (4 μm) were fixed in 2% paraformaldehyde for 5 minutes and allowed to dry overnight at 4° C. followed by extended storage at −20° C. or immunohistochemical detection of monocytes using rat monoclonal α-CD11b (Cedar Lane laboratories, Hornby, Ontario) and Goat anti rat Alexa 488 (Molecular Probes, Inc. Eugene, Oreg.) antibodies at 1:100 and 1:200 dilutions respectively. Sections were cover slipped with vectorshield mounting medium (Vector Corp. Burlingme, Calif.). Approximately ten pictures were taken for each of three sections at least 100 micrometers (μm) apart using an Olympus BH2-RFCA microscope complete with green and red filters. Green fluorescence alone as well as co-localized dual fluorescence were measured using Image Pro Plus software (Media Cybernetics, Inc. Silver Spring, Md.).

ADC568 Labeled Monocyte Transplant

Seven-week old DKO mice were given an iv injection of Alexa 568 conjugated dextran (ADC568) labeled monocytes isolated from either α1 integrin deficient or wild type mouse bone marrow. Bone marrow was collected by flushing the marrow cavities of the femura and tibiae with Dulbecco's Modified EagleMedium (DMEM) supplemented with 2% fetal calf serum (FCS) and Penicillin/Streptomycin. Wash cells 2× in 1× phosphate-buffered saline (PBS) (or Hanks' Balanced Salt Solution (HBSS)). Red blood cells were removed with ammonium chloride (20 mM Tris, 140 mM $NH_4Cl$, pH 7.2) followed by 2 washes in DMEM with 2% FCS and a final wash with HBSS. Cells were cultured for 24 hours in DMEM supplemented with 2% FCS, Pen/Strep at 37° C. in a humidified chamber with 5% $CO_2$. Cells were washed 2× with HBSS and 125 μg ADC568/ml of fresh culture medium were added. Washed cells were resuspended in ADC568 solution and incubate for 24 hours at 37° C. in a humidified chamber with 5% $CO_2$ (try to minimize prolonged exposure to light). Cells were washed 3× with HBSS. Cells were counted and a cell sample prepared to confirm ADC568 labeling with fluorescent microscope. Labeled monocytes were injected into recipient DKO mice via tail vein injection (mice were injected with an equal amount of α1 integrin-null or Wild type monocytes). Kidneys were harvested from recipient mice 72 hours post tail vein injection. Fresh frozen blocks were prepared and cut into 4 μm non-consecutive sections for visualization with fluorescent scope and analysis with Image Pro Plus.

α1β1 integrin/CD31 cDNA Library and Phage Display

Preparation of Recombinant VLA1 coated metallic beads: M450 metallic beads (DYNAL Inc., Lake Success, N.Y.) were coated with recombinant protein according to the manufacturers protocol. Briefly, $1 \times 10^8$ beads were washed in phosphate buffer (0.26 g $NaH_2PO_4$, 1.44 g $Na_2HPO_4$ in 100 mL $ddH_2O$, pH 7.4) using a magnetic chamber. Beads (/$10^7$ beads/5 mg protein) were mixed with 50 kg purified human α1β1 integrin (Chemicon International, Inc., Temecula Calif.) and placed on a nutator at 37° C. for 16 hours. Beads were washed, 2× in buffer D {PBS: 0.88 g NaCl, 0.26 g $NaH_2PO_4$, 1.44 g $Na_2HPO_4$ in 100 ml $ddH_2O$, pH 7.4 with 0.1% BSA} for 5 minutes at 4° C., 1× in buffer E {0.2M Tris pH 8.5 with 0.1% BSA} for 4 hours at 37° C. Beads were stored at +4° C. in buffer D. Incubate cells with α1β1 integrin coated beads in buffer D supplemented with 1 mM $MgCl_2$ and 1 mM $CaCl_2$ for 30 minutes at 4° C.

Preparation of anti-CD31 magnetic beads: Streptavidin linked metallic beads (DNase I recognition domain linker) (DYNAL Inc., Lake Success, N.Y.) were washed in phosphate buffer and combined with biotinylated anti-CD31 antibody (ABCAM, Ltd., Cambridgeshire UK) at 1.0 g/$1 \times 10^7$ beads. The metallic bead/anti-CD31 mixture was placed on a nutator at room temperature for 30 minutes. Following the incubation, beads were washed 2 s in phosphate buffer followed by an additional wash in buffer D. Beads were stored 4° C.

Isolating mRNA from VLA1 binding mouse kidney endothelial cells: Four DKO mice were given a lethal dose of avertin at 10 weeks of age. Animals were perfused with ice cold PBS. Kidneys were harvested and immediately placed on ice in HBSS (Gibco BRL). Kidneys were minced and digested in 20 mL (4 minced kidneys digested in 20 mL Collagenase A) of a 1 milligram per milliliter (mg/mL) Collagenase A (Roche Diagnostics Corp., Indianapolis, Ind.) HBSS solution at 37° C. for 45 minutes with gentle agitation. Digested material was filtered through 70 cm nylon mesh and collected in 50 mL conicle tubes.

Cells were recovered from the digest (1000 revolutions per minute (rpm) for 5 minutes (min) at room temperature) and washed 2× in PBS followed by a final wash in buffer D. The yield from the tissue digest was resuspended in 6 mL of buffer D for every 20 mL of Collagenase A. One milliliter (1 mL) of cell suspension was combined with $1 \times 10^7$ anti-CD31 metallic beads and mixed on a nutator for 30 minutes at 4° C. Rosetted cells were washed 4× in PBS with 0.1% BSA. The metallic beads were liberated from the isolated endothelial cells by incubating rosettes for 15 minutes at room temperature in DNase solution (releasing buffer). Endothelial cells were resuspended in PBS with 0.1% BSA, combined with VLA1 conjugated metallic beads then kept at 4° C. with nutation for 30 minutes. Rosetted cells were washed 4× in PBS with 0.1% BSA. Each wash was saved and unbound endothelial cells were sedimented, resuspended in lysis buffer (Ambion Inc., Austin Tex.) and mRNA extracted. After the final wash, rosetted cells were resuspended in lysis buffer (Ambion Inc, Austin Tex.). After 5 minutes at room temperature, metallic beads were removed and mRNA extracted from the VLA1 binding endothelial cells.

Preparing cDNA Library in T7 Select Phage using Orient express (Novagen, Inc., Madison Wis.): Superscript III (Invitrogen, Corp., Carlsbad Calif.) Reverse transcriptase and methylated dNTPs were used along with HIND III Random primers (Novagen, Inc., Madison W) to generate cDNA that is indigestible with restriction enzymes. Standard dNTPs and T4 DNA polymerase was used to generate flush digestible ends on the Methylated cDNA and ligated to EcoRI/HIND III linkers, followed by digestion with HINDIII and EcoRI restriction enzymes. The digested product was filtered through a size fractionation column (Novagen, Inc., Madison Wis.) and cDNA larger than 300 base pairs (bp) was collected. The collected cDNA was then ligated to T7 select vector arms for preparation of the phage library using T7 select phage packaging extract (Novagen, Inc., Madison Wis.) and the number of recombinants was determined by plaque assay using bacterial strain BLT5403 (Novagen, Inc., Madison Wis.). Following the plaque assay, the phage libraries were amplified by plate lysate amplification, eluted with extraction buffer (20 millimolar (mM) Tris-HCL, pH 8.0, 100 mM NaCl, 6 mM $MgSO_4$), tittered and prepared for long-term storage at −70° C. by addition of 0.1 volume of sterile 80% glycerol.

The complete synthesis of the CD31/VLA1 cDNA phage library was confirmed by PCR using T7 select primers, the following reagents: 10 μL phage lysate; 5 μL 10× NOVATAQ with $MgCl_2$ buffer (Novagen); 1 μL T7 select up primer (GGAGCTGTCGTATFCCAGTC (SEQ ID NO:3)); 1 μL T7 select down primer (AACCCCTCAAGACCCGTFTA (SEQ ID NO:4)); 1 μL dNTP mix (10 mM each); 1.25U NOVATAQ DNA polymerase (Novagen); and qs to 5 μL with PCR grade water. The reaction was heated to 80° C. for two minutes followed by 94° C. for 50 seconds (sec), 50° C. for 1 min, and 72° C. for 1 min for 35 cycles. The final extension was at 72° C. for 6 minutes.

Biopanning for VLA1 binding expressed protein sequence: 96 well high bond plastic plates were coated with recombinant human α1β1 integrin (VLA1) at 5 μg/mL in coating buffer (0.035M $NaHCO_3$, 0.015M $Na_2CO_3$) overnight at 4° C. After coating with VLA1 wells were washed 3× with 1×20 mM Tris.Cl (pH 7.4)_0.5M NaCl (TBS), blocked with 5% nonfat milk TBS buffer then washed 5× with distilled water. Based on the calculated titer of the amplified phage libraries, $8×10^8$ (VLA1-CD31) and $5.9×10^8$ (CD31) phage preps were added to VLA1 coated wells in 200μ 1L biopanning buffer (10 mM Tris-HCl at pH 8.0, 0.15M NaCl, 0.1% Tween-20, 1 mM $MgCl_2$, 1 mM $CaCl_2$) and kept at room temperature for 45 minutes. Wells were washed 5× with biopanning buffer and bound phage were eluted with elution buffer (20 mM Tris at neutral pH, 1.0% SDS) for 20 minutes. BLT5403 bacterial cells were then added to the coated wells to recover high affinity phage that may not have been collected in the eluate. Ninety percent (90%) of the eluted phage were combined with 50 ml bacterial cell culture at $OD_{600}=0.5$ and amplified for three hours at 37° C. with shaking. The remaining 10% was used to determine the number of phage recovered from each round of biopanning. Amplified phage from each round of biopanning was tittered by plaque assay. The biopanning procedure was repeated 3× with $1×10^8$ phage/VLA1 coated well and no more than two coated wells for each library being screened for a total of 4 rounds of biopanning.

PCR and sequencing of VLA1 selected plaques: Amplified phage libraries collected after fourth round of biopanning were diluted sufficiently to generate no more than 100 pfu/plate. Twelve individual plaques were scraped and plugs of each plaque scraped were collected for each library. One milliliter phage extraction buffer was added to each plug and stored at 4° C. Plaques collected by scraping top agarose with a pipette tip were dispersed in 100 μL of 10 mM EDTA, pH 8.0, vortexed and kept at 65° C. for 10 minutes. Samples were cooled to room temperature and centrifuged at 14000×g for 3 minutes.

PCR was run using the following reagents: 2 μL clarified phage lysate; 5 μL 10× TAQ Gold Buffer (Perkin Elmer); 5 μL 25 mM $MgCl_2$; 1 μL T7 select up primer (GGAGCTGTCGTATTCCAGTC (SEQ ID NO:3)); 1 μL T7 select down primer (AACCCCTCAAGACCCGTTTA (SEQ ID NO:4)); 1 μL dNTP mix (10 mM each); 0.5 μL TAQ Gold DNA polymerase (Perkin Elmer); and qs to 5 μL with PCR grade water. The reaction was heated to 94° C. with DNA polymerase for 2 minutes followed by 94° C. for 50 sec, 50° C. for 1 min, and 72° C. for 1 min for 35 cycles. The final extension was at 72° C. for 6 minutes.

Ten microliters (10 μL) of the PCR reaction were run on a 1% agarose gel prepared with TAE (40 mM Tris, 10 mM EDTA, 20 mM glacial acetic acid) and EtBr (10 μg/ml). The remaining PCR reaction was adjusted to 150 μL with distilled water. This was transferred to MANU 030 plate and the plate was vacuum dried for 20 minutes. The PCR product was recovered by adding 4 μL nanopure water to the appropriate wells in the plate. Five microliters (5 μL) of product was mixed with 1 μL of either forward or reverse primer, 2μΛ Ready Reaction Mix (Applied Biosystems Inc., Foster City, Calif.) and 2μΛ of 5× Buffer (Applied Biosystems Inc).

After cycle sequencing, 40 μL of 70% ethanol (EtOH) were added and the mixture incubated at room temperature for 15 minutes. The mixture was then centrifuged for 30 minutes at 3400 rpm, caps to PCR tubes were removed, tubes inverted, and spun briefly (1 minute) at 1000 rpm. The precipitated product was allowed to dry for 30 minutes to 1 hour. The products were resuspended in formamide loading dye solution, the mixture incubated at 96° C. for 3 minutes, placed on ice for 2 minutes, then samples were loaded onto sequencing gel within 15 minutes of adding formamide solution.

Endothelial cell MCP-1 $H_2O_2$ Experiment

Primary endothelial cells were isolated from wild type mouse kidneys using anti-CD31 coated metallic beads. Cells were cultured in endothelial cell medium (DMEM/F12, 50 μg/ml Endothelial mitogen, 1% penicillin/streptomycin, 20 mM L-Glutamine, and 1 U/mL heparin prepared fresh not filtered) containing 20% FCS. Thirty-two wells of $5×10^4$ cells/well in a 96 well plate coated with 1% gelatin in sterile PBS were set up. Cells were maintained in endothelial cell media with 20% FCS until cells reached confluence. Confluent cells were washed with HBSS, then covered with endothelial cell media without serum at 200 μL/well and kept in a humidified chamber at 37° C., 5% $CO_2$. Twenty-four hours later fresh endothelial cell medium was added without serum and various concentrations of MCP-1 and $H_2O_2$ were added at 24 or 48 hours (hrs) prior to conducting the assay for cell binding to α1β1 integrin as shown in the following Table 1.

TABLE 1

| Control | 800 μM $H_2O_2$ 48 hrs | 200 pg MCP-1 24 hrs | 100 μM $H_2O_2$ 24 hrs | 800 pg MCP-1 48 hrs | 50 μM $H_2O_2$ 48 hrs |
|---|---|---|---|---|---|
| Control | 800 μM $H_2O_2$ 24 hrs | 1200 pg MCP-1 24 hrs | 100 μM $H_2O_2$ 24 hrs | 1200 pg MCP-1 48 hrs | 50 μM $H_2O_2$ 48 hrs |

TABLE 1-continued

| Control | 800 µM $H_2O_2$ 24 hrs | 1600 pg MCP-1 24 hrs | 100 µM $H_2O_2$ 24 hrs | 1200 pg MCP-1 48 hrs | 100 µM $H_2O_2$ 48 hrs |
|---|---|---|---|---|---|
| Control VLA1 | 800 µM $H_2O_2$ 24 hrs | 1600 pg MCP-1 24 hrs | 200 µM $H_2O_2$ 24 hrs | 1200 pg MCP-1 48 hrs | 100 µM $H_2O_2$ 48 hrs |
| Control VLA1 | 800 pg MCP-1 24 hrs | 1600 pg MCP-1 24 hrs | 200 µM $H_2O_2$ 24 hrs | 1600 pg MCP-1 48 hrs | 100 µM $H_2O_2$ 48 hrs |
| Control VLA1 | 800 pg MCP-1 24 hrs | 50 µM $H_2O_2$ 24 hrs | 200 µM $H_2O_2$ 24 hrs | 1600 pg MCP-1 48 hrs | 200 µM $H_2O_2$ 48 hrs |
| 800 µM $H_2O_2$ 48 hrs | 800 pg MCP-1 24 hrs | 50 µM $H_2O_2$ 24 hrs | 800 pg MCP-1 48 hrs | 1600 pg MCP-1 48 hrs | 200 µM $H_2O_2$ 48 hrs |
| 800 µM $H_2O_2$ 48 hrs | 1200 pg MCP-1 24 hrs | 50 µM $H_2O_2$ 24 hrs | 800 pg MCP-1 48 hrs | 50 µM $H_2O_2$ 48 hrs | 200 µM $H_2O_2$ 48 hrs |

Immunoprecipitation

Endothelial cell cultures were grown to confluency and placed in serum free endothelial cell medium for 24 hours. Cells were then treated with 1600 pigograms (pg) human recombinant MCP-1 or 200 µM $H_2O_2$ for 48 hours under serum free conditions. Cells were washed 2× with ice cold HBSS and cell were sonicated on ice (10× for 15 sec pulses) in integrin lysis buffer (50 mM Hepes pH 7.4, 100 mM NaCl, 0.4% Triton X-100, 1 mM $CaCl_2$, 1 mM $MgCl_2$, 10% glycerol) with protease inhibitors. Protein concentrations were determined by Bradford Assay (BioRad). Equal concentrations of lysates were pre-cleared with protein-A sepharose beads. Recombinant human VLA1 (0.2 µg) was added to the pre-cleared lysates and incubated at 4° C. for 1 hour followed by addition of rabbit anti VLA1 antibody (Chemicon) and protein-A sepharose beads. Samples were incubated over night at 4° C. with nutation. Beads were washed 6× with integrin lysis buffer and protease inhibitors at 4° C. then combined with 50 µL 6× Laemmli sample buffer, boiled for 5 minutes and kept on ice.

Samples were run on 10% SDS PAGE gels and transferred to PVDF membrane (BioRad). Membrane was incubated overnight at 4° C. with Collagen XIII antibody, raised in rabbit against a synthetic peptide of the NC3 domain provided by Dr. Taina Pihlajaniemi (Hagg et al., J. Biol. Chem. 273, 15590-15597), diluted 1:2000 in 1% BSA, 0.05% Tween 20_20 mM Tris.Cl (pH 7.4)_0.5M NaC (TTBS). The membrane was washed several times in TTBS the incubated with Goat anti rabbit-HRP was diluted 1:25000 in 1% BSA TTBS for 1 hour. Bands were detected with chemiluminescence detection kit (Amersham) and X-ray film.

RT-PCR

Total RNA was prepared using Trizol (GibCo/BRL, Gaithersberg, Md.) as per the manufacturer's instructions. Two micrograms of total RNA was reverse-transcribed by using a first strand cDNA synthesis kit SuperScript III (GibCo BRL). Collagen XIII mRNA transcripts were analyzed semi-quantitatively using specific primers by RT-PCR. As an internal standard, expression of glyceraldehydes 3-phosphate dehydrogenase (GAPDH), a cellular housekeeping gene, was also analyzed. PCR reactions were carried out in PTC 100 (M.J. Research, Waltham, Mass.) using amplitaq gold (Applied Biosystems, Branchburg, N.J.) with 1 cycle of 94° C. for 2 min, 30 cycles of 94° C. for 60 sec, 60° C. for 60 sec, 72° C. for 90 sec followed by 72° C. for 10 min, then held at 4° C. Oligonucleotide primer pairs used are listed below in Table 2.

TABLE 2

| Primer pair | | Target size (bp) |
|---|---|---|
| GAPDH | 5'-GGT GAA GGT CGG AGT CAA CGG ATT TGG TCG-3' (SEQ ID NO: 5) 5'-GGA TCT CGC TCC TGG AAG ATG GTG ATG GG-3' (SEQ ID NO: 6) | 236 |
| Collagen XIII | 5'-GAGCGGGGCATGCCAGGAAT-3' (SEQ ID NO: 7) 5'-TGGCCATCAACACCAGCTTC-3' (SEQ ID NO: 8) | 254 |
| Collagen XIII | 5'-CTGCGCTCCAACCCGATAATGTCC-3' (SEQ ID NO: 9) 5'-CTGGGGGCCTGCTTGTCCTGTCT-3' (SEQ ID NO: 10) | 880 |

Primers were designed based on the published sequences. Amplified products were separated on 2% agarose gel, visualized by UV transilluminator after staining with ethidium bromide, and photographed. All PCR experiments included control reactions, which contained all components except complementary DNA. No bands were detectable in these control reactions. All PCR products were confirmed by DNA sequencing.

Immunofluoresence.

Four-micron fresh frozen kidney sections were mounted on slides and fixed with ice-cold acetone. Tissue sections were examined by immunofluorescence microscopy using primary antibodies specific for endothelial cells (anti-mouse CD31, (Abcam)) or Collagen XIII (gift from Dr. TainaPihlajaniemi (Hagg et al., J. Biol. Chem. 273, 15590-15597) at a concentration of 1:100 and 1:200 in 1% BSA, 5% mouse serum, 1×PBS respectively. Kidney sections were incubated in primary antibody for 60 minutes, washed 3× with 1×PBS then incubated with anti-rabbit Alexa fluor 568 (red-colXIII), anti-rat Alexa fluor 488 (green-CD31) (Molecular Probes, Inc. Eugene, Oreg., USA) each prepared in 1% BSA, 5% Mouse serum, 1×PBS at a concentration of 1:200 for 60 minutes. After washing 3× with 1×PBS, mounting medium (0.1 g N-propyl-gallate, 5 ml 1×PBS, 5 ml glycerol) was added and the samples were coverslipped.

Immunostaining was visualized and captured with an Olympus BH2-RFCA fluorescent microscope (Hitschfel Instruments Inc., St. Louis, Mo.) mounted with a SPOT-RT-Slider imaging system and software (Diagnostic Instruments Inc., Sterling Heights, Mich.) at 200× magnification.

Results

Monocyte efflux into Alport kidneys is mediated via an endothelial cell surface ligand for integrin α1β1.

In an earlier report (Sampson et al., J. Biol. Chem., 276, 34182-34188 (2001)), it was shown that the number of monocytes and myofibroblasts present in the kidneys of Alport mice that are also null for integrin α1β1 (DKO's) is much lower than that for age matched Alport mice. While this data certainly indicated a role for α1β1 integrin in fibrosis, it did not clarify the mechanism(s) underlying the observation.

While numerous possible explanations exist (α1β1 integrin effects on chemokine/cytokine expression by tubular epithelial cells or downstream effects of slowed glomerular pathology, for example), the direct role for α1β1 integrin in monocyte efflux into the tubulointerstitium was explored. The monocytes in the Alport tubulointerstitium were predominantly positive for α1β1 integrin (FIG. 1). This may reflect recruitment of α1β1 integrin-positive monocytes from the peripheral blood, or activation of α1β1 integrin expression in monocytes following entry into the tubulointerstitial space.

Figure 2:
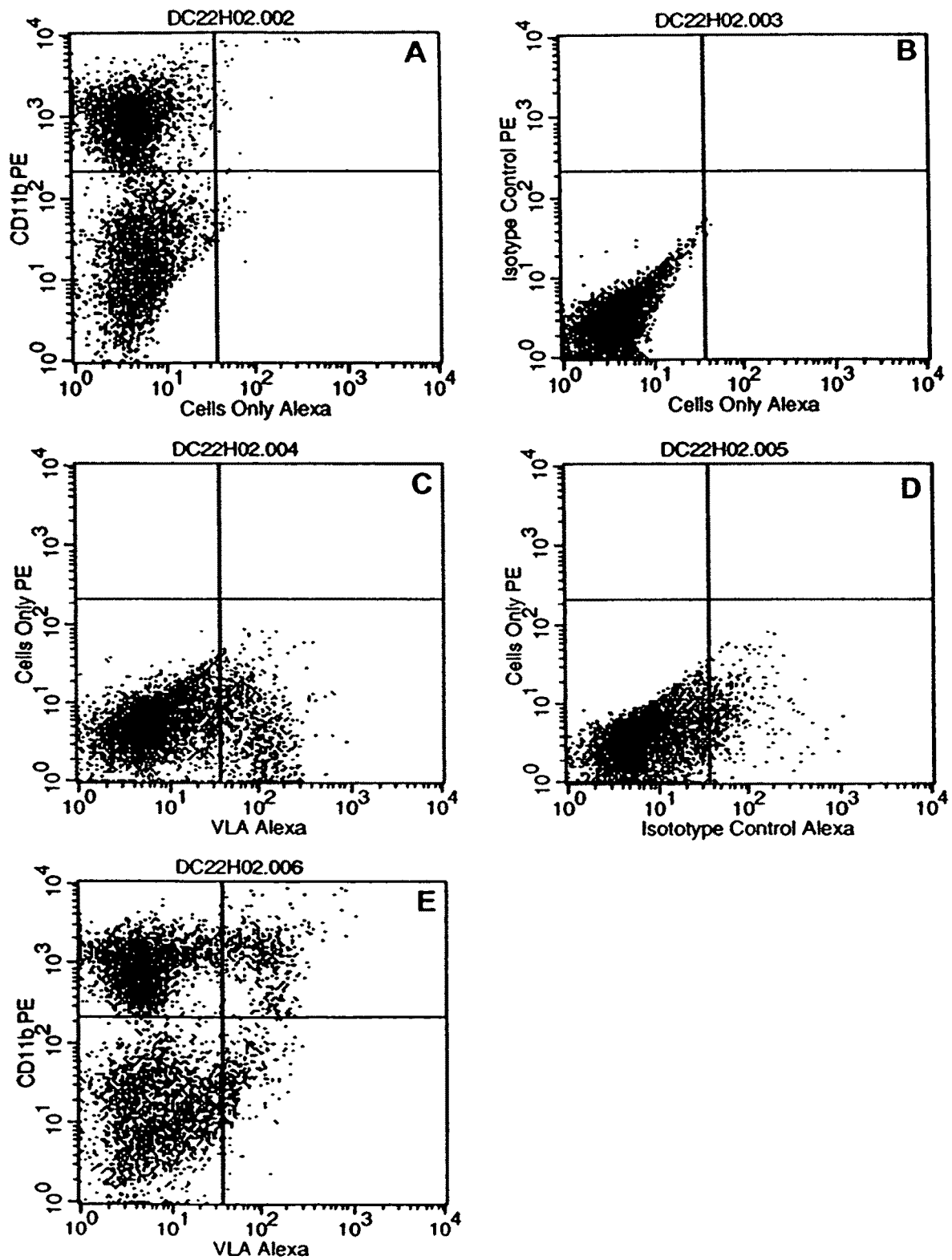
FIGS. 2A-2E. About 10% of bone marrow-derived monocytes express integrin α1β1. Fluorescence activated cell sorting (FACS) using antibody markers for monocytes (CD11bPE) and integrin α1β1 (VLA Alexa), and isotype matched control antibodies were used for two color analysis of bone marrow-derived lymphocytes. About 10% of the CD11b-positive cells were also positive for integrin α1β1 (FIG. 2E, double-positive cells in the upper right hand quadrant of the histogram).
Figure 3:
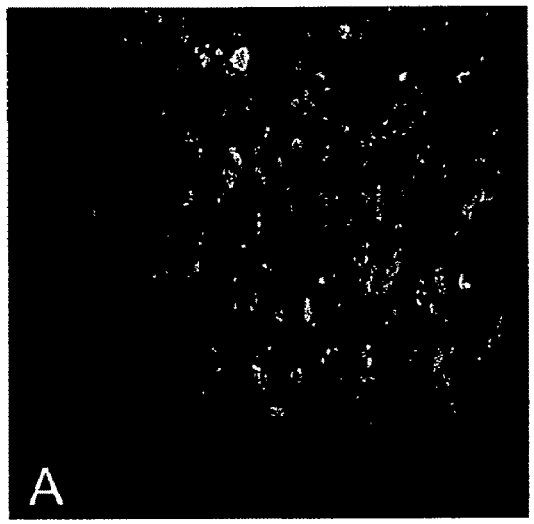
FIGS. 3A-3D. Tail vein injection of Alexa 568-labeled dextrans allows trafficking of CD11b-positive monocytes; all monocytes recruited to the tubulointerstitium of Alport mice are positive for integrin α1β1. A 7-week-old Alport mouse was injected with 1 μg of Alexa-568-conjugated dextrans. Three days following the injection, kidneys were harvested, embedded in OCT aqueous embedding media, and cryosectioned. Tissue sections were immunostained with either FITC-conjugated anti integrin α1β1-specific antibodies (FIG. 3C), or FITC-conjugated anti-CD11b antibodies (FIG. 3A). The results clearly indicate that the Alexa-labeled cells newly infiltrated into the Alport tubulointerstitium are all monocytes, and are all integrin α1β1-positive.
Figure 3:
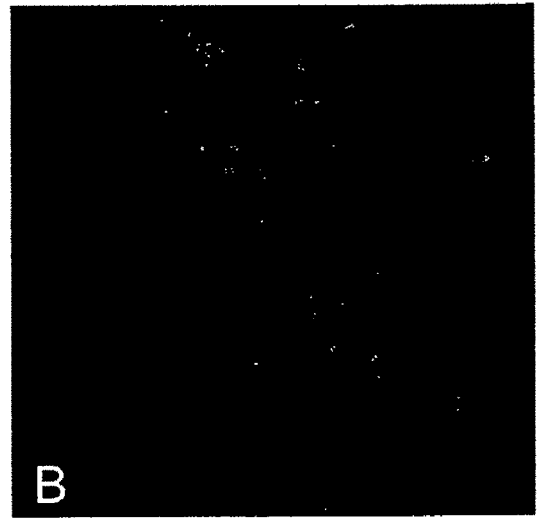
Figure 3:
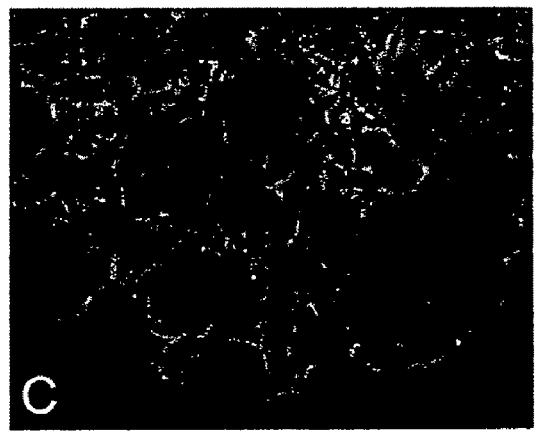
Figure 3:

Bone marrow-derived monocytes were analyzed by fluorescence-activated cell sorting (FACS), using fluorescence-tagged antibodies against CD11b (a marker for monocytes, fluorescence intensity monitored on the Y-axis of histograms in FIG. 2) and α1β1 integrin (fluorescence intensity monitored along the X-axis of histograms in FIG. 2). The results shown in FIG. 2 illustrate that a fraction (about 10%) of the monocytes in bone marrow express α1β1 integrin. To determine whether newly effluxed monocytes express α1β1 integrin, dextrans were labeled with Alexa 568 (red fluorescence tag from Molecular Probes). Since monocytes are the only phagocytic cells in the peripheral blood, only monocytes are labeled when these dextrans are injected into the tail vein. Three days following injection, kidneys were harvested and cryosections immunostained with FITC-conjugated (green) anti-CD11b antibody. The results in FIGS. 3A and 3B show that Alexa-labeled cells are monocytes. A second section was immunostained with FITC-conjugated anti α1β1 integrin antibody. FIGS. 3C and 3D illustrate that Alexa-labeled cells are immunopositive for α1β1 integrin. Combined, these data illustrate the specificity of the labeled dextran approach for monitoring monocyte trafficking into the tubulointerstitium, and illustrate that newly effluxed monocytes express α1β1 integrin, supporting the possibility for a direct role for this integrin in facilitating entry into the tubulointerstitial space.

Figure 4:
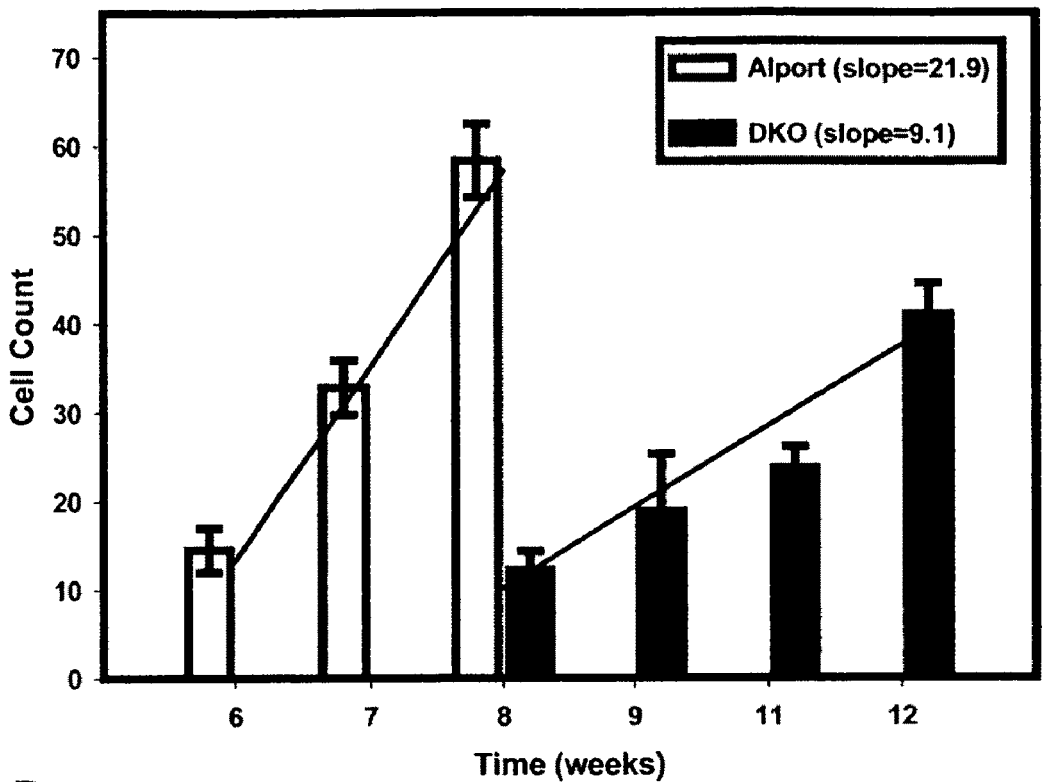
FIGS. 4A and 4B. Monocyte efflux is delayed, and the rate of monocyte efflux is reduced in the renal cortex of integrin α1β1-deficient Alport mice relative to Alport mice. Blocking this ligand using purified α1β1 integrin may reduce the rate of monocyte efflux into the interstitium.
Figure 4:
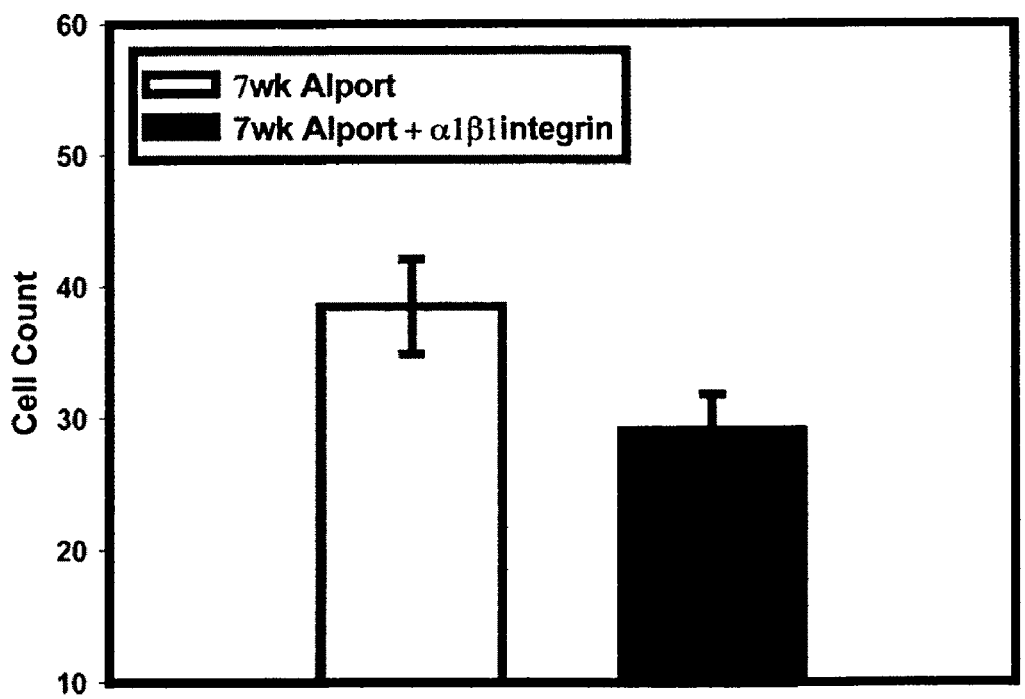

If α1β1 integrin mediates monocyte efflux, then the rate of efflux in Alport mice should be faster than that for α1β1-deficient Alport (DKO) mice. These two models were injected with labeled dextrans in a timecourse study. Three days following injection, kidneys were harvested and immunostained with FITC-conjugated anti-CD11b. Labeled monocytes were counted in 20 fields for 10 sections 100 μM apart. Two independent animals were used for each timepoint. The results in FIG. 4 show that the onset of monocyte efflux in the DKO mice is much later than that in Alport mice. More importantly, the rate at which monocytes are entering the tubulointerstitial space is much slower in the DKO mice relative to the Alport mice, providing further evidence for a direct role for α1β1 integrin in mediating monocyte efflux into the tubulointerstitium. Bars in FIG. 4 represent standard error, not standard deviation. Because monocyte efflux is patchy, fields representing the entire peripheral renal cortex of a longitudinal cryosection are imaged and counted.

Figure 5:
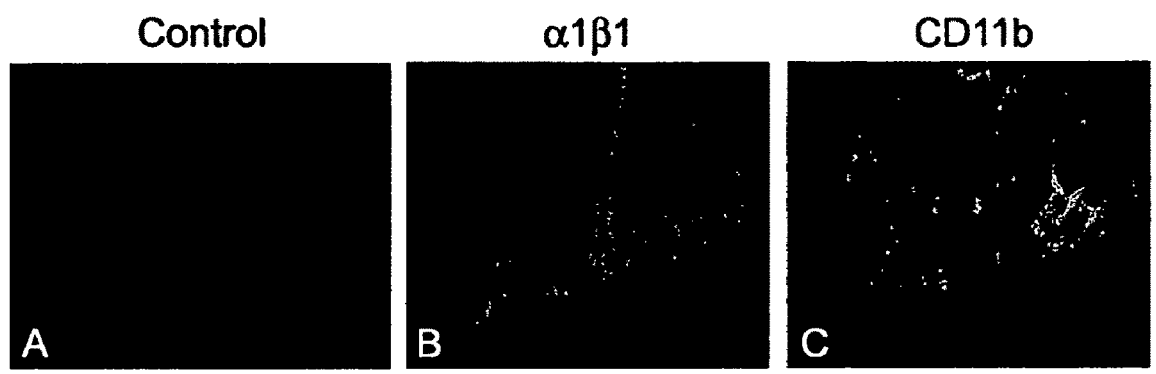
FIGS. 5A-5C. α1β1 integrin binds the vascular endothelium of Alport kidneys, but not normal kidneys. Purified α1β1 integrin was conjugated to Alexa 568 fluorochrome and injected in to the tail vein of normal (A) and Alport (B) mice. After 24 hours, kidneys were harvested, cryosectioned, and imaged using a fluorescence microscope.

If such a direct role exists, there must be a ligand for α1β1 integrin on the renal cortical vascular endothelium of Alport mice that is absent on normal mice. To test for the presence of such a ligand, purified α1β1 integrin (purchased from Chemicon, Temecula, Calif.) was labeled with Alexa 568, and the labeled integrin injected into the tail vein of normal, Alport, and DKO mice. Twenty-four hours following the injection, kidneys were harvested, and cryosections examined. The results in FIG. 5A illustrate the absence of label in control mice, while Alport mice show strong labeling in the vascular endothelium (FIG. 5B). Since monocytes phagocytize labeled dextrans, what is interpreted as integrin might be phagocytized integrin in monocytes. Comparing FIGS. 5B and % C shows that monocytes and Alexa-labeled integrin α1β1 do not co-localize (since there is no overlapping fluorescence in the two panels). These data illustrate the presence of a ligand for α1β1 integrin in Alport vascular endothelium. Its presence in age matched DKO mice further suggests the absence of α1β1 integrin in these mice may explain the slowed rate of monocyte efflux.

In an attempt to provide a more definitive test for the function of α1β1 in monocyte efflux into diseased kidneys, 5 μg of purified α1β1 integrin was injected into the tail vein of Alport mice daily, starting one day before injection of labeled dextrans, and kidneys harvested three days following injection of dextrans. Pilot studies with Alexa-conjugated integrin α1β1 were conducted to assess the stability prior to the blocking experiments. The purified integrin was found to be stable for at least 72 hours (data not shown). If transendothelial migration of monocytes into the interstitial space is mediated, in part, through binding a ligand on endothelial cells, a decrease in labeled monocytes in Alport mice treated with α1β1 integrin compared to untreated age-matched Alport mice should be observed, since the purified integrin should occupy ligand, making less available for binding to monocytes. The results in FIG. 4B illustrate a trend for a reduction in monocyte efflux for mice treated with the purified α1β1 integrin. It suggests that the ligand may indeed function in recruitment of monocytes to the interstitial space in Alport kidneys.

To further test whether the influence of α1β1 integrin on peripheral blood monocytes facilitates transmigration into the interstitial space of fibrosing kidneys, a transplantation approach was used. Irradiation and chemical myoloablation strategies proved toxic in the Alport mouse, accelerating fibrosis. A passive transplantation approach was chosen where bone marrow derived monocytes from either normal controls or α1 integrin null mice were labeled by culturing cells in the presence of Alexa-568 fluorochrome-conjugated dextrans. The labeled cells were injected into integrin α1-deficient Alport (DKO) mice and the rate of transendothelial migration assessed by counting fluorescent cells in the interstitium three days following transplantation. Table 3, below, shows the results for 5 independent experiments. While the numbers varied from one experimental set of animals to another, in all cases there was a significant reduction in the number of transmigrated monocytes in mice transplanted with integrin α1-deficient monocytes compared to those transplanted with normal monocytes.

TABLE 3

| ADC568 labeled monocytes injected into DKO mice. | Experiment 1 | | Experiment 2 | | Experiment 3 | | Experiment 4 | | Experiment 5 | |
|---|---|---|---|---|---|---|---|---|---|---|
| | WT | $\mu L^{-/-}$ | WT | $\mu L^{-/-}$ | WT | $\mu L^{-/-}$ | WT | $\mu L^{-/-}$ | WT | $\mu L^{-/-}$ |
| Number of cells injected | $2.5 \times 10^6$ | | $3.0 \times 10^6$ | | $3.0 \times 10^6$ | | $2.0 \times 10^6$ | | $2.0 \times 10^6$ | |
| Number of cells/3 sections | 190 | 103 | 338 | 299 | 934 | 773 | 351 | 265 | 260 | 233 |

TABLE 3-continued

| ADC568 labeled monocytes injected into DKO mice. | Experiment 1 | | Experiment 2 | | Experiment 3 | | Experiment 4 | | Experiment 5 | |
|---|---|---|---|---|---|---|---|---|---|---|
| | WT | μL$^{-/-}$ | WT | μL$^{-/-}$ | WT | μL$^{-/-}$ | WT | μL$^{-/-}$ | WT | μL$^{-/-}$ |
| Percentage of cells in kidney | 0.0076 | 0.00412 | 0.011 | 0.0099 | 0.031 | 0.026 | 0.018 | 0.013 | 0.013 | 0.012 |
| Percent reduction (μL$^{-/-}$) | 45.8 | | 10 | | 16.1 | | 27.8 | | 7.7 | |

Cloning and identification of the vascular endothelial cell ligand for integrin α1β1, Collagen XIII.

The data presented thus far predicts that a ligand for α1β1 integrin is expressed on vascular endothelial cells of kidneys during progressive fibrosis. While a number of approaches were pursued to clone the ligand, a biopanning approach of a kidney endothelial cell-specific phage display library was successfully used. Endothelial cells from α1 integrin deficient Alport mice were isolated using antibodies conjugated to magnetic beads. Kidneys were minced and treated with collagenase to free cells from interstitial matrix. The cells were mixed with magnetic beads that were chemically conjugated to a commercially available antibody specific for endothelial cells (anti-CD31). Bound cells were separated from unbound cells using a magnet, and washed several times. The resulting cells were either used directly to prepare RNA or further selected using magnetic beads conjugated to purified α1β1 integrin, then used for RNA preparation. The two different RNA preparations were subjected to poly-A selection, and the PolyA+ RNA used to construct a filamentous phage display library. The filamentous phage is engineered to display a small portion of cloned cDNAs as peptides on one end of the filament. Specific interacting peptides can be selected using an approach referred to as "biopanning." Plastic micotiter plates are coated with the protein for which interactive binding partners are sought (in this case, this is purified α1β1 integrin). The library of phage is then allowed to react to the coated plate under conditions that typically promote integrin/ligand interactions. Phage that fail to react are washed away, and the bound phage eluted and amplified. This process is repeated several times in serial, which after three or more successive binding and amplification steps results in the purification of phage that specifically interact with the protein used to coat the plates. In this case, only a single phage clone was purified using this technique. DNA sequence analysis of the insert revealed that the phage was presenting a fragment of Collagen XIII, which is a plasma membrane bound collagen (Hagg et al., J. Biol. Chem., 273, 15590-15597, 1998). Interestingly, the only receptor that has been shown to bind to Collagen XIII is α1β1 integrin (Nykvist et al., J. Biol. Chem., 275, 8255-8261, 2000). The biological function of the Collagen XIII/α1β1 interaction is completely unknown, but is thought to have something to do with cell/cell adhesion. It should be emphasized that, by virtue of the mechanics of the phage display assay, Collagen XIII has been identified as the endothelial cell ligand for α1β1 integrin. Because of the small size of the inserted DNA in the phage that is homologous to Collagen XIII, the binding site for α1β1 integrin has also been identified. This is a significant fact, since it allows for the testing of the efficacy of peptide inhibitors comprising this amino acid sequence. The amino acid sequence of the cloned fragment (i.e., the portion of Collagen XIII involved in binding α1β1 integrin is as follows: GEKGAEGSPGLL (SEQ ID NO:2).

Collagen XIII is induced on vascular endothelial cells from chronically inflamed kidneys.

Figure 6:
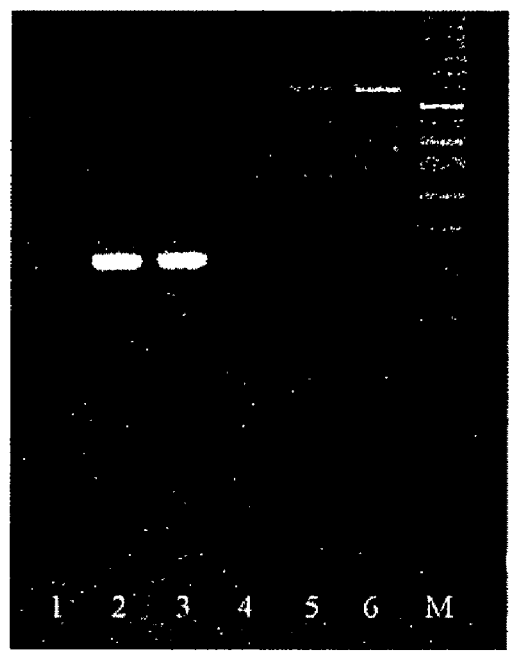
FIG. 6. Collagen XIII mRNA is induced in vascular endothelial cells from Alport mice compared to controls. Endothelial cells were isolated from wild type and Alport kidneys then RNA extracted. Reverse transcribed RNA with oligo dT primers. PCR amplified with GAPDH (lanes 1-3) and Collagen XIII-880 bp (lanes 4-6). Lane 1: Water control GAPDH; Lane 2: Wild type GAPDH; Lane 3: Alport GAPDH; Lane 4: Water control Col XIII; Lane 5: Wild type Col XIII; Lane 6: Alport Col XIII; and Lane M: 100 bp ladder.

Endothelial cell polyA+ mRNA was prepared from normal and 7-week-old Alport (advanced fibrotic) kidneys as described above and analyzed for Collagen XIII expression using RT-PCR. As shown in FIG. 6, expression of Collagen XIII is induced in vascular endothelial cells of Alport kidneys relative to normal mice. Parallel reactions amplified GAPDH, a housekeeping gene, as a control. GAPDH transcripts were very similar in the two samples.

Figure 7:
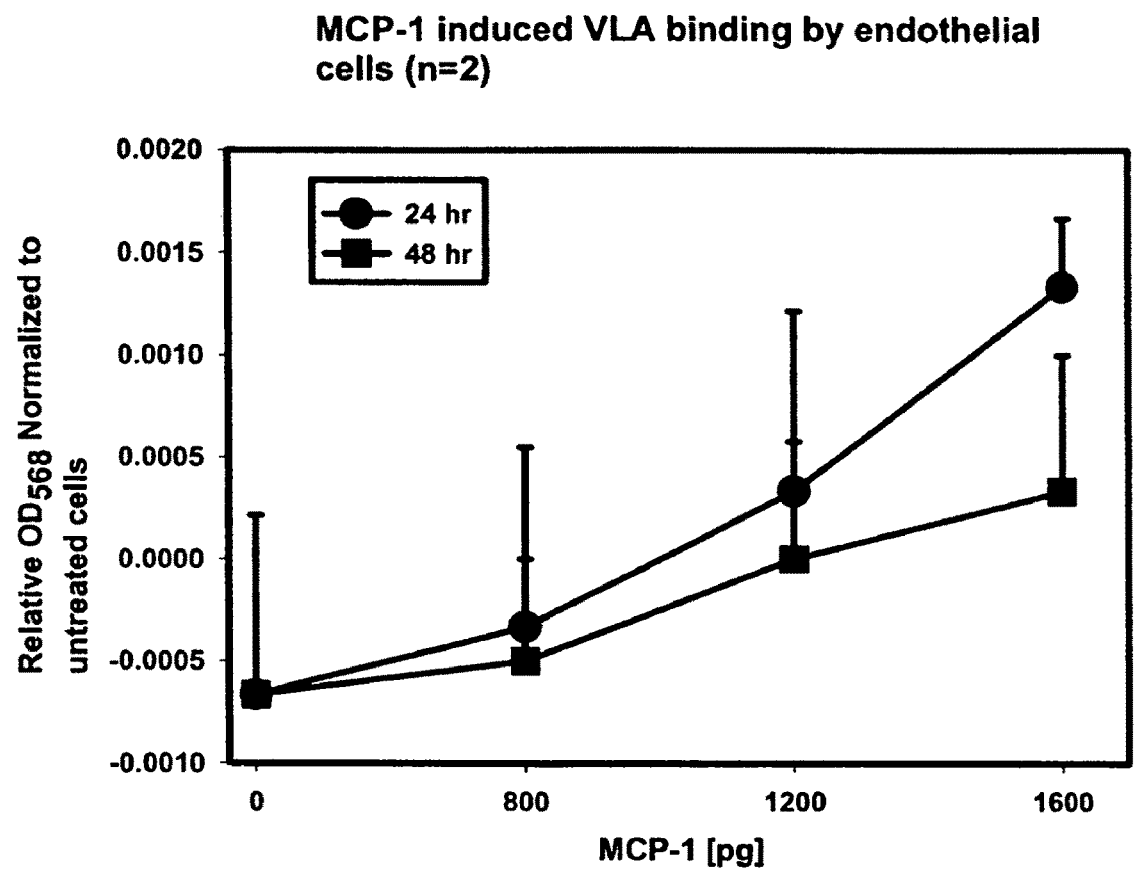
FIG. 7. MCP-1 promotes endothelial cell binding of VLA1 recombinant protein in vitro. Cultured primary endothelial cells from mouse kidneys were treated with the indicated concentrations of recombinant MCP-1. Triplicate wells were analyzed for the capacity to bind to purified fluorochrome-conjugated integrin α1β1. Data represents the mean and standard deviation for three independent experiments.

It has been previously shown that monocyte chemo-attractive protein-1 (MCP-1) is markedly induced in Alport kidneys relative to normal kidneys (Sampson et al., J. Biol. Chem., 276, 34182-34188 (2001)). There is wide documentation for the capacity of this powerful chemokine to promote monocyte and lymphocyte transmigration into the interstitium of inflamed tissues (reviewed in Conti et al., Allergy Asthma Proc., 22, 133-7 (2001)). This is thought to be mediated largely through the induction of adhesion molecules and/or their respective ligands (Kim, J. Neurol. Sci., 137, 69-78 (1996)). Based on this, primary kidney endothelial cell cultures were treated with varying concentrations of recombinant MCP-1 and measured adhesion to Alexa-568-conjugated α1β1 integrin. FIG. 7 illustrates significantly elevated adhesion of α1β1 integrin to endothelial cells pre-treated with MCP-1 compared to untreated cells. The increased adhesion was both time and dose dependent.

Figure 8:
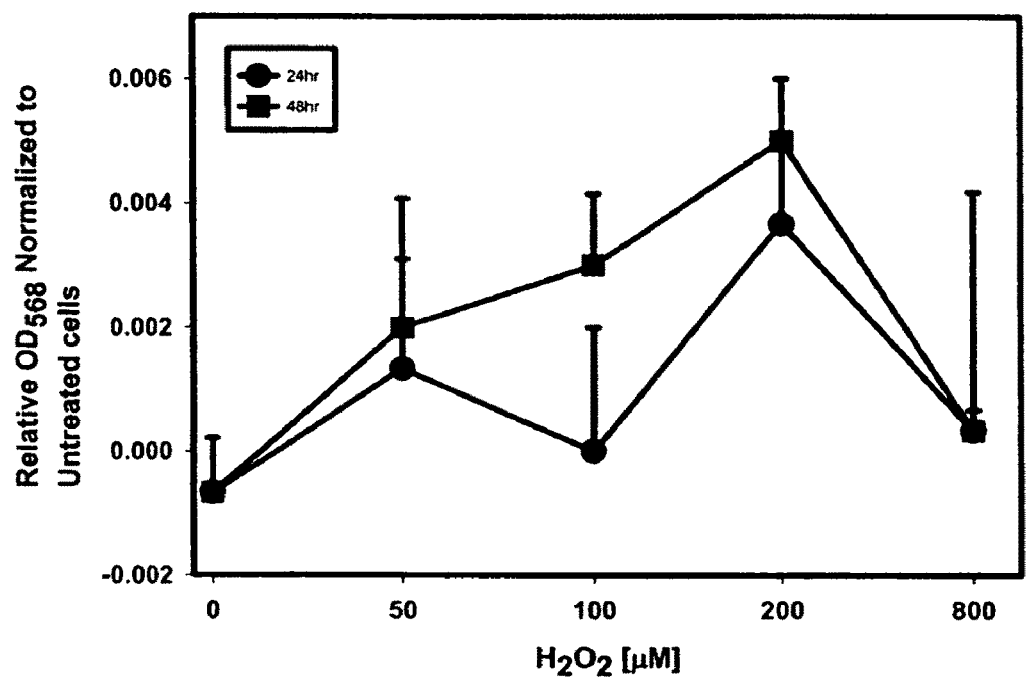
FIG. 8. Hydrogen peroxide promotes endothelial cell binding of VLA1 recombinant protein in vitro. Cultured primary endothelial cells from mouse kidneys were treated with the indicated concentrations of hydrogen peroxide. Triplicate wells were analyzed for the capacity to bind to purified fluorochrome-conjugated integrin α1β1. Data represents the mean and standard deviation for three independent experiments.

In addition to chemokines, oxidative stress has been associated with the induction of cytokines, matrix proteins, metalloproteinases, and cell adhesion molecules in the endothelium of inflammatory tissues (Yoon et al., 2002 J. Biol. Chem., 277, 30271-30282); Roebuck, Int. J. Mol. Med., 4, 223-30 (1999)). In vivo, this is largely due to elevated expression of endothelial nitric oxide synthetase (eNOS) and inducible nitric oxide synthetase (iNOS), which leads to the production of hydrogen peroxide (Heering a et al., J. Pathology, 193, 224-32 (2001). In FIG. 8, it is illustrated that hydrogen peroxide promotes the binding of Alexa-conjugated α1β1 integrin to cultured primary kidney endothelial cells. This effect is both concentration and time-dependent.

Figure 9:
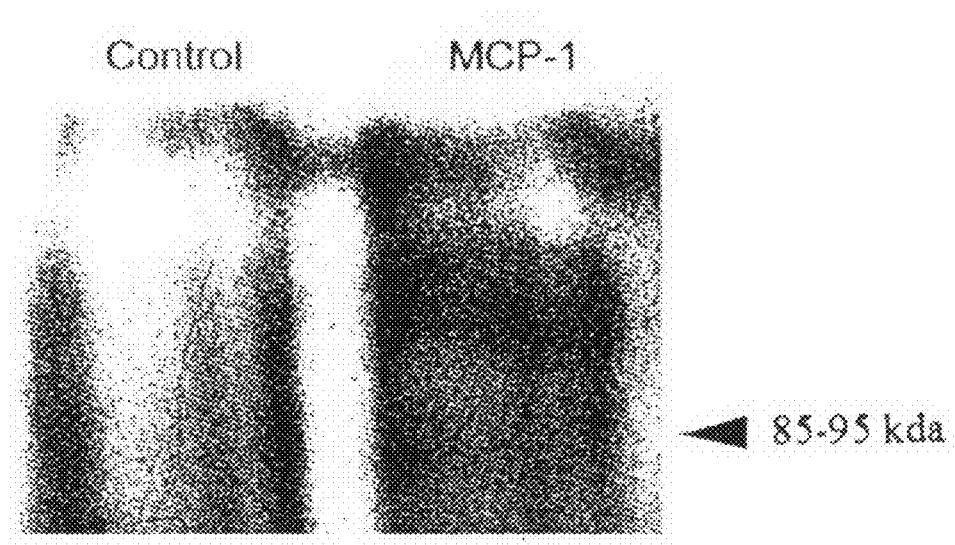
FIG. 9. Indirect immunoprecipitation of Collagen XIII from cultured renal endothelial cells. Either untreated or MCP-1 treated primary endothelial cells were subjected to indirect immunoprecipitation analysis. Cells were lysed and purified α1β1 integrin added to the lysate. Complexes were immunoprecipitated with anti-α1 integrin antibodies. The immunoprecipitate was analyzed by western blot probed with anti-collagen XIII antibodies. The expected bands for Collagen XIII (93 and 115 kilodaltons, respectively) are denoted with arrowheads.

To determine whether the α1β1 integrin binding activity on cultured vascular endothelial cells was indeed Collagen XIII, an indirect co-immunoprecipitation assay was performed. Endothelial cells were cultured in the presence or absence of MCP-1 for 48 hours. The cells were lysed in integrin binding buffer, and purified integrin α1β1 added to the cleared mix. Following incubation, anti-integrin α1-specific antibodies were added, and complexes immunoprecipitated with protein A sepharose beads. The immunoprecipitated material was fractionated by polyacrylamide gel electrophoresis (PAGE) and analyzed by western blot using anti-collagen XIII antibodies. The results in FIG. 9 illustrate one bands with the appropriate molecular size for type XIII collagen (between 85 and 95 kDa) consistent with earlier reports (Hägg et al., J. Biol. Chem. 273, 15590-15597 (1998); Hägg et al., Matrix Biology, 19, 727-742 (2001)).

Figure 10:
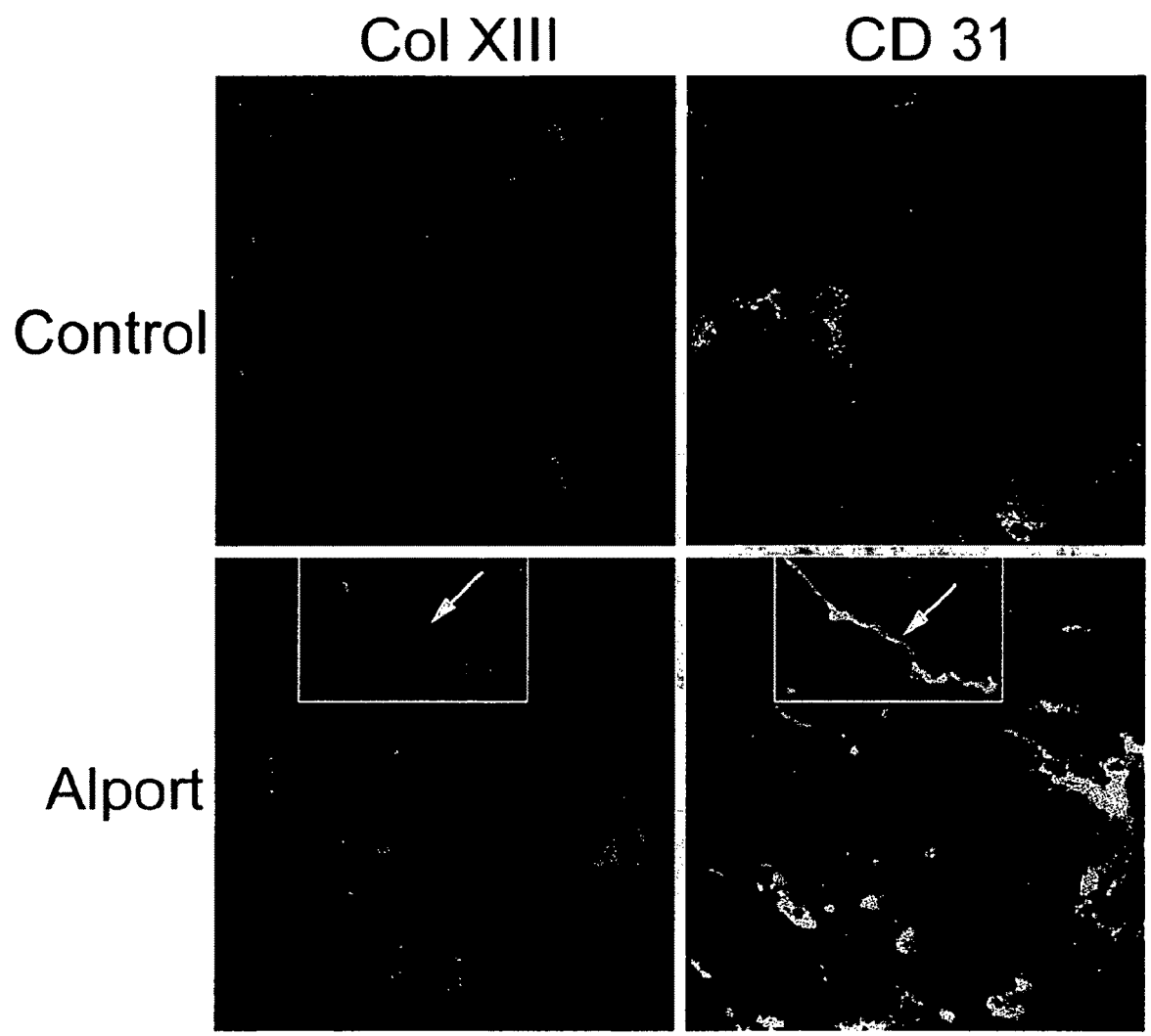
FIG. 10. Collagen XIII co-localizes with the vascular endothelial cells marker CD31 in Alport kidneys, but not normal kidneys. Immunofluorescence analysis was performed on kidney cryosections from normal controls and Alport mice using antibodies against either Collagen XIII or CD31. In the boxed in regions is an area where Collagen XIII is clearly lining up with the vascular endothelium. These regions were only observed in fibrosing kidneys.

To determine whether Collagen XIII is induced on the vascular endothelium in vivo, dual immunofluorescence analysis of kidney cryosections from normal and Alport mice was performed using antibodies specific for Collagen XIII and CD31 (a specific endothelial cell marker). The data shown in FIG. 10 illustrates areas of obvious co-localization for Collagen XIII and CD31 in the Alport renal cortex (boxed in areas). No co-localization for these two proteins was observed in controls.

Discussion

Previous work has shown that the progression of interstitial fibrosis was slower in integrin α1 null Alport (DKO) mice than Alport mice of the same inbred background (129 Sv) (Cosgrove et al., Am. J. Path., 157, 1649-1659 (2000); Rodgers et al., Kidney Int., 63, 1338-1355 (2003). This work was extended in related studies using both the integrin α1 null mouse model (Gardner et al., Dev. Biol., 175, 301-313 (1999)) and a neutralizing antibody approach to be effective in slowing the rate of progression for other inflammatory diseases including rheumatoid arthritis (De Fougerolles et al., The Journal of Clinical Investigation, 105, 721-729 (2000)), crescentic glomerulonephritis (Cook et al., Am. J. Path., 161, 1265-1272 (2002)), and experimental colitis (Krieglstein et al., J. Clin. Invest., 110, 1173-1782 (2002)). While the beneficial effect of integrin α1β1 neutralization was significant in all cases, the mechanism underlying these observations was not known.

Studies performed aimed at defining the relative roles of monocytes and myofibroblasts in interstitial destruction overwhelmingly concluded that the tissue monocytes mediate apoptosis of kidney cells contributing to the tissue destruction associated with progressive renal fibrosis (Rodgers et al., Kidney Int., 63, 1338-1355 (2003)). Herein it is shown that the accumulation of interstitial monocytes in integrin α1-null Alport mice is markedly attenuated compared to that in Alport mice. This slowed rate of accumulation may be due to a decrease in the rate at which monocytes efflux into the interstitial space and/or an influence on interstitial monocyte proliferation. In this application it was demonstrate via injection of fluorochrome conjugated dextrans that the rate at which monocytes efflux into the interstitial space is much slower in integrin α1-deficient Alport mice compared to Alport mice. Indeed, the fluorochrome-labeled monocytes observed in the Alport interstitium in this assay were predominantly integrin α1β1-positive cells. Transplant studies using fluorochrome labeled cultured monocytes from the bone marrow of wild type and integrin α1-deficient mice confirm a significant reduction in the rate of efflux when injected into α1 integrin-deficient Alport mice, directly demonstrating that integrin α1β1 on peripheral blood monocytes enhances their rate of transendothelial migration into the interstitial space of chronically inflamed kidneys.

Given this, and additional supporting evidence, it was surmised that there must be a ligand for α1β1 integrin on the endothelial cell surface of Alport kidneys undergoing active fibrosis. Injection of fluorochrome-conjugated purified α1β1 integrin into the tail vein of Alport, integrin α1-deficient Alport, and normal control mice confirmed that the integrin adheres to the vascular endothelium of the diseased mice, but not the normal mice. A phage display approach for identifying interacting proteins (Ruoslahti et al., Cancer Biology, 10, 435-442 (2000); Laakkonen et al., Nature Medicine, 8, 751-755 (2002)) was used to identify Collagen XIII as the endothelial cell receptor for α1β1-positive peripheral blood monocytes. Collagen XIII is a plasma membrane collagen (Hägg et al., J. Biol. Chem., 273, 15590-15597 (1998)). It has been characterized as a specific ligand for α1β1 integrin (Nykvist et al., J. Biol. Chem., 275, 8255-8261 (2000)), but the functional role of the interaction has remained unclear. Interestingly, the amino acid sequence of the Collagen XIII peptide identified in our phage display assay is homologous (67% identity in amino acid sequence) to the collagenous domain of a class A scavenger receptor, which has been identified as a mechanism for macrophage adhesion to collagens (Gowen et al., J. Leuk. Biol., 69, 575-582 (2001); Kosswig et al., J. Biol. Chem., 278, 34219-34225 (2003)).

A previous report suggested that collagen binding integrins α1β1 and α1β1 are involved in transmigration of activated T-cells into inflammatory tissues, but the cellular mechanism mediating this effect was not addressed (Andreasen et al., J. Immunol., 171, 2804-2811 (2003)). In humans with arthritis, integrin α1β1-positive lymphocytes were found to be a subset of T-cells primed for adhesion to type IV collagen (Bank et al., Clinical Immunol., 105, 247-258 (2002)), suggesting a specific role for α1β1-positive lymphocytes in promoting chronic inflammation in humans.

The studies presented herein bring these concepts together, offering an explanation for how inflamed tissues select this subpopulation of circulating monocytes and lymphocytes. The biological reason for selecting these cells for transmigration however remains a mystery. It is possible that activation of these cells via α1β1 integrin signaling imparts characteristics normally beneficial to resolving the inflammatory state. It was observed that while inflammation-associated monocytes were immunopositive for TGF-β1, resident monocytes were not (Rodgers et al., Kidney Int., 63, 1338-1355 (2003)). While acute elevations may be beneficial to resolving an inflammatory state, sustained exposure to elevated TGF-β is notoriously destructive (Border et al., Nature (London), 346, 371-374 (1990)).

While the biological reason for this mechanism remains unclear, the potential therapeutic benefit of blocking α1β1 integrin-mediated transmigration of lymphocytes/monocytes for controlling tissue destruction associated with chronic inflammatory disorders, based on the work described in this application, is apparent. The transplantation data presented herein show that α1β1 neutralization has a significant, albeit marginal effect on monocyte transmigration into the renal interstitium. Clearly there are other mechanisms driving the infiltration of monocytes in this chronic inflammatory model. Directed therapeutic paradigms aimed at limiting lymphocyte/monocyte transmigration have been effective at slowing the progression of chronic inflammatory disorders such as psoriasis, inflammatory bowel disease and multiple sclerosis in humans (Harlan et al., Crit. Care Med., 30, S214-9 (2002)). Some of the better-characterized approaches involve the blocking of both the receptor and its ligand usually via neutralizing monoclonal antibodies. This approach has been successfully applied to LFA-1/ICAM-1 interaction (suppressing efflux of leukocytes into inflammatory tissues) and the VLA-4/VCAM-1 interaction (suppressing efflux of lymphocytes and monocytes into inflammatory tissues) (Yusuf-Makagiansar et al., Med. Res. Rev., 22, 146-67 (2002)). Recently, a new adhesion molecule expressed on endothelial cells, vascular adhesion protein-1 (VAP-1), was implicated as playing a key role in adhesion and transmigration of lymphocytes associated with chronic inflammation of the liver (Lalor et al., J. Immunol., 169, 983-92 (2002)). Combined, this body of research underscores the diversity of mechanisms influencing the binding, activation, and efflux of inflammatory cells into sites of chronically inflamed tissues.

Given the evidence provided herein, it is obvious that the integrin α1β1/Collagen XIII interaction plays an important role in mediating efflux of monocytes into chronically inflamed kidneys. Studies employing α1β1 integrin-specific neutralizing antibodies and/or integrin α1-deficient mice implicate that this mechanism is involved in rheumatoid arthritis, crescentic glomerulonephritis, and experimental colitis. This therapeutic approach will likely provide benefit for any chronic inflammatory disease where α1β1 integrin-positive lymphocytes/monocytes are involved.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

Sequence Free Text

SEQ ID NO:1 Peptide

SEQ ID NO:2 Peptide

SEQ ID NO:3 Primer

SEQ ID NO:4 Primer

SEQ ID NO:5 Primer

SEQ ID NO:6 Primer

SEQ ID NO:7 Primer

SEQ ID NO:8 Primer

SEQ ID NO:9 Primer

SEQ ID NO:10 Primer

What is claimed is:

1. An antibody that binds to a peptide fragment of Collagen XIII, said peptide fragment of Collagen XIII consisting of 8 to 16 amino acid residues and said peptide fragment of Collagen XIII having SEQ ID NO:1.

2. The antibody of claim 1, said peptide fragment of Collagen XIII consisting of SEQ ID NO:1.

3. The antibody of claim 1, said peptide fragment of Collagen XIII consisting of SEQ ID NO:2 or said peptide fragment of Collagen XIII consisting of SEQ ID NO:2 with a deletion of one amino acid from one or both termini.

4. The antibody of claim 1, wherein said antibody is a monoclonal antibody.

5. The antibody of claim 1, wherein said antibody blocks the interaction of $\alpha 1\beta 1$ integrin on peripheral blood monocytes and/or lymphocytes with Collagen XIII on vascular endothelium.

6. The antibody of claim 1, wherein said antibody inhibits the binding of fluorochrome-conjugated $\alpha 1\beta 1$ integrin to MCP-1 treated primary endothelial cells in culture.

* * * * *